(12) United States Patent
Hatamoto et al.

(10) Patent No.: US 7,842,799 B2
(45) Date of Patent: Nov. 30, 2010

(54) RECOMBINANT VECTOR CAPABLE OF INCREASING SECRETION OF KOJI MOLD PROTEASE

(75) Inventors: Osamu Hatamoto, Noda (JP); Genryou Umitsüki, Chiba (JP); Masayuki Machida, Ibaraki (JP); Motoaki Sano, Ishikawa (JP); Akimitsu Tanaka, Choshi (JP); Chitoshi Oka, Chiba (JP); Hiroshi Maeda, Miyagi (JP); Hitoshi Tainaka, Chiba (JP); Touru Ito, Chiba (JP); Tomomi Uchikawa, Chiba (JP); Tsutomu Masuda, Chiba (JP); Kenichiro Matsushima, Chiba (JP)

(73) Assignees: Noda Institute for Scientific Research, Noda-shi (JP); Kikkoman Corporation, Noda-shi (JP)

( * ) Notice: Subject to any disclaimer, the term of this patent is extended or adjusted under 35 U.S.C. 154(b) by 102 days.

(21) Appl. No.: 11/990,926

(22) PCT Filed: Sep. 19, 2006

(86) PCT No.: PCT/JP2006/318508

§ 371 (c)(1),
(2), (4) Date: Jun. 30, 2008

(87) PCT Pub. No.: WO2007/034782

PCT Pub. Date: Mar. 29, 2007

(65) Prior Publication Data

US 2009/0130711 A1    May 21, 2009

(30) Foreign Application Priority Data

Sep. 26, 2005  (JP)  ............... 2005-278095

(51) Int. Cl.
*C12N 15/31* (2006.01)
*C12N 15/79* (2006.01)
*C12N 15/80* (2006.01)

(52) U.S. Cl. .............. 536/23.74; 435/69.1; 435/254.11; 435/254.3; 435/320.1; 530/358

(58) Field of Classification Search ............. None
See application file for complete search history.

(56) References Cited

U.S. PATENT DOCUMENTS

| | | | |
|---|---|---|---|
| 6,090,607 | A | 7/2000 | Van Den Broek et al. |
| 2004/0082053 | A1 | 4/2004 | Machida et al. |

FOREIGN PATENT DOCUMENTS

| | | |
|---|---|---|
| JP | 2001-500022 A | 1/2001 |
| JP | 2002-101888 A | 4/2002 |
| JP | 2003-240 A | 1/2003 |
| JP | 2003-70484 A | 3/2003 |
| JP | 2003-235584 A | 8/2003 |
| JP | 2005-176602 A | 7/2005 |

OTHER PUBLICATIONS

Machida, M., et al., Dec. 2005, "Genome sequencing and analysis of *Aspergillus oryzae*", Nature, vol. 438, pp. 1157-1161.*

(Continued)

*Primary Examiner*—Manjunath N Rao
*Assistant Examiner*—William W Moore
(74) *Attorney, Agent, or Firm*—Birch, Stewart, Kolasch & Birch, LLP

(57) ABSTRACT

To improve the activity of a Koji mold protease in a solid or liquid culture medium in the production of foods (e.g., a seasoning), pharmaceuticals (e.g., a digestive agent), protease for use in a detergent and the like.

Disclosed are a recombinant vector having capability of increasing the secretion of the Koji mold protease, a Koji mold which is transformed with the vector and has an increased expression of a gene for a protease or an increase secretion of the same, a method for the production of a protease by using the transformed Koji mold, and the like.

9 Claims, 1 Drawing Sheet

OTHER PUBLICATIONS

Database Embl 1998, XP002503912, Database accession No. AF080600.
Database Embl 2001, XP002503913, Database accession No. AF284062.
Database Embl 2001, XP002503914, Database accession No. AAF11955.
Akimitsu Tanaka, "Koujikin *Aspefillus oryzae* Yurai Alkaline Protease Idenshi no Hatsugen Kiko no Kaiseki" The Society for Biotechnology, Japan Taikai Koen Yoshishu, Aug. 24, 2001, p. 370, No. 953.
S. Cheevadhanarak, Cloning and selective overexpression of an alkaline protease-encoding gene from *Aspergillus oryzae*, Gene (1991), vol. 108, pp. 151-155.
Database EMBL, Jun. 18, 2004, "EST836955 *Aspergillus flavus* Normalized cDNA Expression Library *Aspergillus flavus* cDNA clone NAFEN88 5' end, mRNA sequence" XP002568754 retrieved from EBI accession No. EMBL:C0142284.
Database EMBL, Mar. 13, 1997, "*Emericella nidulans* DNA binding regulatory protein AmdX (amdX) gene, complete cds.", XP002568751 retrieved from EBI accession No. EMBL:U56100.
Database Geneseq, Mar. 28, 2003, "*Aspergillus oryzae* polynucleotide SEQ ID No. 2520.", XP002568753 retrieved from EBI accession No. GSN:ABZ53407.
Database Geneseq. Nov. 4, 2004, XP002568752 retrieved from EBI accession No. GSN:ADR84958.
European Search Report issued on Mar. 4, 2010 for European Application No. 09010747.5.

* cited by examiner

[Fig. 1]
Southern analysis of the strain compulsorily expressing C001 gene
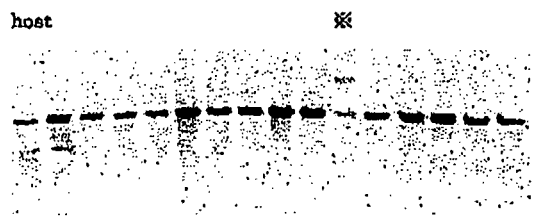
Southern analysis of the strain compulsorily expressing C002 gene
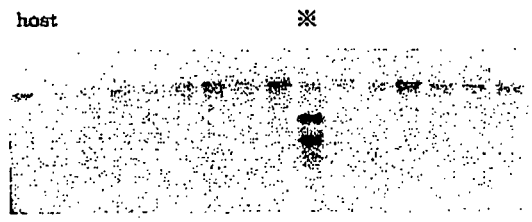
Southern analysis of the strain compulsorily expressing C003 gene
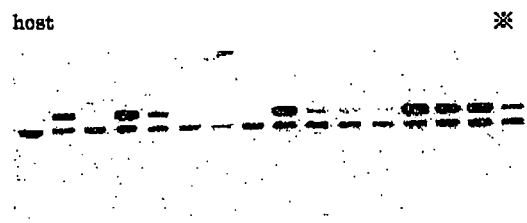
Southern analysis of the strain compulsorily expressing C004 gene
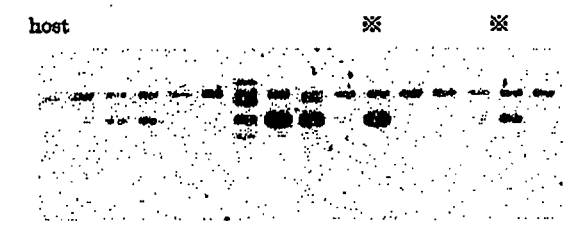
host : RIB326niaD-strain    ※ : selected strains
[Fig. 2]
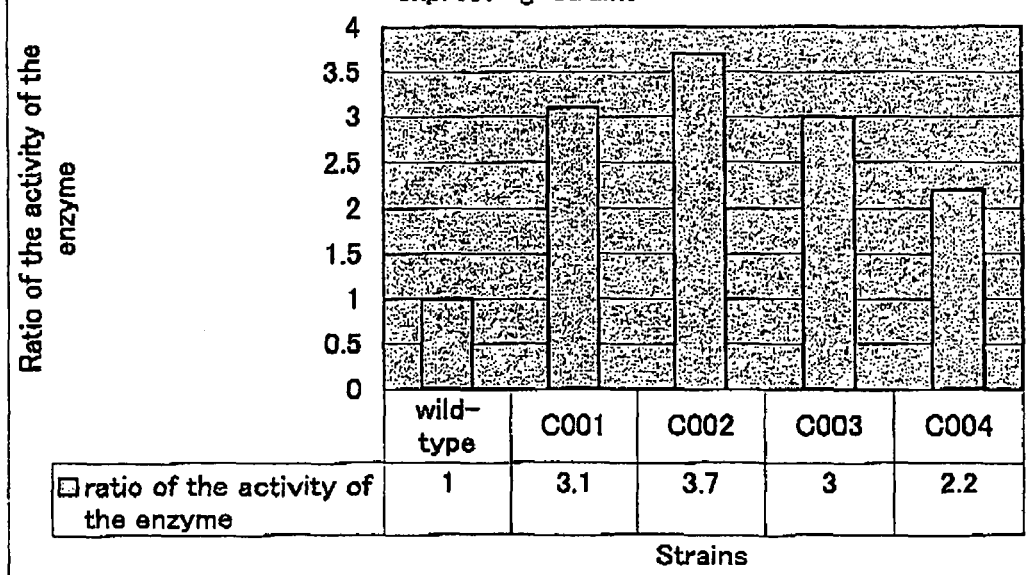

RECOMBINANT VECTOR CAPABLE OF INCREASING SECRETION OF KOJI MOLD PROTEASE

The present application is the national stage application of PCT Application No. PCT/JP2006/318508, which was filed on Sep. 19, 2006. PCT/JP2006/318508 claims the benefit of priority of Japanese Application No. 2005-278095, which was filed on Sep. 26, 2005.

TECHNICAL FIELD

The present invention relates to a recombinant vector having a capability of increasing the secretion of a protease (protein hydrolase) of Koji mold (*Aspergillus* strains), Koji mold transformed with the vector having an increased expression of a gene for the protease and an increased secretion of the protease, and a method for the production of a protease by using the transformed Koji mold, etc.

BACKGROUND OF THE INVENTION

Koji mold such as *Aspergillus oryzae* and *Aspergillus sojae* have been industrially used in the production of brewed foods such as soy sauce, sake (rice wine), soybean paste, etc. Recently, a genome sequence of *Aspergillus oryzae* was identified (Japanese Patent Application Publication No. 2005-176602), and functionally analysis of their genes has become more important.

As the Koji mold produces and secretes a variety of enzymes such a protease (protein hydrolase) and an amylase, and has an excellent capability of starch saccharifing and proteolysis, it has been widely utilized in the production of brewed foods.

Analyses were made for various transcriptional factors controlling the expression of the genes of the Koji mold, as described in the following patent publications.

[Patent Document 1] Japanese Patent Application Publication 2003-240

[Patent Document 2] Japanese Patent Application Publication 2003-70484

[Patent Document 3] Japanese Patent Application Publication 2003-235584

[Patent Document 4] Japanese Patent Application Publication 2005-176802

Problems to be Solved by of the Invention

The purpose of the present invention is to provide a recombinant vector having a capability of increasing the secretion of a protease of Koji mold, and Koji mold having an improved efficiency of the degradation of protein-containing materials in a solid or liquid culture medium, etc.

Means for Solving the Problems

Thus, the present invention relates to the following aspects.
(1) A recombinant vector comprising a DNA consisting of a nucleotide sequence represented by SEQ ID NO:1, 2, 3 or 4.
(2) A recombinant vector comprising a DNA being hybridized under stringent conditions with a DNA consisting of a nucleotide sequence complementary with that of the DNA consisting of a nucleotide sequence represented by SEQ ID NO:1, 2, 3 or 4, and encoding a protein having a capability of increasing the secretion of a protease of Koji mold (*Aspergillus* strains).
(3) A recombinant vector comprising a DNA consisting of a nucleotide sequence showing identity of 80% or more with that represented by SEQ ID NO:1, 2, 3 or 4, and encoding a protein having a capability of increasing the secretion of a protease of Koji mold (*Aspergillus* strains).
(4) A Koji mold introduced or transformed with the recombinant vector of claim 1, 2 or 3, and having an increased capability of the secretion of a protease compared with that of its parent strain.
(5) A method for the production of a protease, comprising culturing the Koji mold of claim 4 in a solid or liquid culture medium to make it secrete the protease into the culture medium, and collecting the protease from the culture medium.
(6) A method for the production of a protein degradation product, comprising mixing a culture material obtained by culturing the Koji mold of claim 4 with a protein-containing material so as to degrade the protein in the material.
(7) A method for the production of a seasoning liquid, comprising mixing a culture material obtained by culturing the Koji mold of claim 4 with a gelatin-containing material so as to degrade the gelatin in the material.
(8) A DNA of the following (a), (b) or (c);
  (a) a DNA consisting of a nucleotide sequence represented by SEQ ID NO:1, 2, 3 or 4;
  (b) a DNA being hybridized under stringent conditions with a DNA consisting of a nucleotide sequence complementary with that of the DNA (a), and encoding a protein having a capability of increasing the secretion of a protease of Koji mold (*Aspergillus* strains);
  (c) a DNA consisting of a nucleotide sequence showing identity of 80% or more with that represented by SEQ ID NO:1, 2, 3 or 4, and encoding a protein having a capability of increasing the secretion of a protease of Koji mold (*Aspergillus* strains).
(9) A protein of the following (a) or (b):
  (a) a protein consisting of an amino acid sequence encoded by a DNA consisting of a nucleotide sequence represented by SEQ ID NO:1, 2, 3 or 4;
  (b) a protein consisting of an amino acid sequence of (a) wherein one or a few amino acid residues are replaced, deleted, or added, and having a capability of increasing the secretion of a protease of Koji mold (*Aspergillus* strains).

Advantages of the Invention

The recombinant vector according to the present invention has made it possible to increase the secretion of the protease of the Koji mold. By using the Koji mold transformed with the recombinant vectors mentioned above, the efficiency of the degradation of protein-containing materials can be increased in a solid or liquid culture material.

BRIEF DESCRIPTION OF DRAWINGS

FIG. 1 is a photo showing the results of electrophoresis obtained in Southern analysis, which shows that a plasmid used in the transformation of a transformant according to the present invention has been inserted at the niaD locus of the genome of the transformant.

FIG. 2 shows the results of comparison of the activity of proteases in a bran medium between a wild-type strain and the transformant according to the present invention.

BEST MODE FOR CARRYING OUT THE PRESENT INVENTION

The DNA consisting of a nucleotide sequence represented by SEQ ID NO:1, 2, 3 or 4, which is comprised in the recombinant vector according to the present invention, is derived from the genome of the Koji mold. It was deduced to be a DNA encoding a transcriptional regulatory gene, based on the whole genome sequence of *Aspergillus oryzae* (Japanese Patent Application Publication No. 2005-176602); homology search; motif search; literature information, annotations and kinds of motifs concerning known genes, as described in the following examples. It may be obtained from the genome DNA of the Koji mold by means of PCR using suitable primers, as described in the following examples.

The "DNA consisting of a nucleotide sequence represented by SEQ ID NO:1, 2, 3 or 4" according to the present invention comprises cDNA consisting of a nucleotide sequence consisting only of a region encoding amino acids, i.e., a nucleotide sequence composed only of exons. Such cDNA may be easily obtained by means of PCR using mRNA of the Koji mold as a template with suitable primers that are prepared based on the nucleotide sequence information disclosed in the present specification. Alternatively, it may be chemically synthesized by any method known by those skilled in the art.

The recombinant vector according to the present invention may also comprise a DNA being hybridized under stringent conditions with a DNA consisting of a nucleotide sequence complementary with that of the above DNA, and a DNA consisting of a nucleotide sequence showing identity (homology) of about 80% or more, preferably about 95% or more with that of the above DNA, and encoding a protein having a capability of increasing the secretion of a protease of Koji mold (*Aspergillus* strains).

The hybridization may be performed in accordance with a method known in the art, for example, that described in Molecular cloning third ed. (Cold Spring Harbor Lab. Press 2001). When a commercially available library is used, the hybridization may be done according to instructions attached to it.

The hybridization may be performed in accordance with a method known in the art, for example, that described in Current protocols in molecular biology (edited by Frederick M. Ausubel et al., 1987). When a commercially available library is used, the hybridization may be done according to instructions attached to it.

The term "stringent conditions" means in this specification, for example, those of sodium concentration of 150~900 mM, preferably 600~900 mM, pH of 6~8 at 60° C.~68° C.

The DNA that is hybridized with DNA consisting of a nucleotide sequence complementary with that of the DNA consisting of the nucleotide sequence represented by SEQ ID NO:1, 2, 3 or 4 may include, for example, DNA comprising a nucleotide sequence having identity of about 80% or more, preferably of about 95% or more on a total average with the whole nucleotide sequence of the DNA of interest. The identity between the nucleotide sequences may be determined by means of algorithm known for those skilled in the art, such as BLAST.

Accordingly, the present invention relates to the DNA comprising the nucleotide sequence represented by SEQ ID NO:1, 2, 3 or 4, to the DNA being hybridized under stringent conditions with the DNA consisting of the nucleotide sequence complementary with that of the DNA of interest, and to the DNA consisting of a nucleotide sequence showing identity of about 80% or more, preferably 95% or more with that represented by SEQ ID NO:1, 2, 3 or 4, and encoding a protein having a capability of increasing the secretion of a protease of the Koji mold; and to the protein consisting of an amino acid sequence encoded by the DNA consisting of the nucleotide sequence represented by SEQ ID NO:1, 2, 3 or 4; and to the protein consisting of the above amino acid sequences and having a capability of increasing the secretion of a protease of the Koji mold.

In order to determine the identity of sequences between two amino acid sequences or two nucleotide sequences, the sequences will be pre-treated to become in an optimum condition for comparison. For example, gaps may be inserted into one of the sequences so that alignment with the other sequence will be optimized. After such pre-treatment, amino acid residues or bases in each region will be compared. When amino acid residues or bases located at a certain position in a first sequence are the same as those of a second sequence located at a position corresponding to the above position in the first sequence, these two sequences will be considered as the same at the position. Identity between the two sequences will be shown by percentage of the number of the amino acid residues or bases that are the same in the two sequences for the number of the whole amino acid residues or bases.

According to the above principle, identity between the two amino acid sequences or nucleotide sequences may be determined, for example, by algorithm of Karlin and Altschul (Proc. Natl. Acad. Sci. USA 87:2 264-2268, 1990; and Proc. Natl. Acad. Sci. USA 990:5873-5877, 1993). BLAST or FASTA programs based on the above algorithms may be used for searching a sequence having a high identity with a given sequence from database. Such programs are available at a Web site of National Center for Biotechnology Information on the Internet.

The DNA showing the above identity in the amino acid sequence or nucleotide sequence may be obtained by resorting to the above hybridization, or may be easily found in public databases or a group of functionally unidentified DNAs obtained with analysis of genome sequences by means of methods conventionally used by those skilled in the art, for example, by searching with the above BLAST software. The gene DNA according to the present invention may be alternatively obtained by any known methods for the introduction of mutation.

The recombinant vector according to the present invention may be prepared by ligating the above DNA into a vector by means of any genetic engineering known for those skilled in the art. There is no limitation on structure, kind and the like of the vector, as long as the DNA will be inserted into an appropriate position in the genome of a host microorganism to be introduced or transformed so that the capability of the secretion of a protease of the host microorganism can be increased compared with that of its parent strain. For example, vectors including a plasmid, cosmid, phage, virus, chromosome integrated type, artificial chromosome, etc.

Any known marker gene may be comprised in the vector for allowing the selection of a transformed cell. The marker gene includes a gene compensating auxotrophy of the host such as URA3 and niaD, a drug-resistance gene such as for ampicillin, kanamycin and oligomycin. The recombinant vector may preferably comprise a promoter that can express the gene according to the present invention in the host cell and other regulatory sequences such as an enhancer sequence, terminator sequence, and polyadenylation sequence as well as a multi-cloning site for the insertion of a target DNA. Each element comprised in the recombinant vector is well known for those skilled in the art, including a promoter for an amylase gene of *Aspergillus oryzae*, an amylase terminator of *Aspergillus nidulans*, niaD gene of *Aspergillus oryzae* as a marker gene, as shown by the examples in the present specification.

Transduction or transformation may be carried out by a known and appropriate method such as that using the treatment of protoplast with polyethyleneglycol and calcium chloride (Mol. Gen. Genet., 218, 99-104 (1989)).

The Koji mold introduced or transformed with the vector of the present invention has an increased secretion of a protease compared with that of its parent strain. The "increase or increased the secretion of a protease" in this specification means that an amount of a protease secreted out of the mold (strain) has been increased as a final result (phenomenon). The reason or mechanism for such increase may be considered to be the increase of an amount of the expression or production per se of the protease and/or the increase of an amount of secretion (secretion capability) of the enzyme produced out of the mold. The "increase" means in this context that the amount of the protease or its activity in the culture medium of the mold transduced or transformed with the recombinant vector of the present invention has been significantly increased compared with that of its parent strain in accordance with a determination method using gelatin or azocasein as a substrate protein.

Accordingly, the protein encoded by each sequence comprised in the vector is predicted to be a transcriptional regulatory factor as described in the following examples. However, it is not limited to one that binds to a transcriptional regulatory element of the protease and is capable of promoting the expression of the protease. It also includes one that is capable of promoting the secretion of the expressed protease out of the mold transduced or transformed with the recombinant vector of the present invention.

The Koji mold is a generic term meaning microorganisms (fungi) belonging to genus *Aspergillus*, which includes *Aspergillus oryzae, Aspergillus sojae*, as well as *Aspergillus awamori* and *Aspergillus niger* that are used in the food and brew industries. Same advantages may be obtained by using other filamentous fungi than the Koji mold, which are used in the fields of food, brew, chemistry and healthcare. Such fungi are commercially available, or may be alternatively obtained from various public depositories such as American Type Culture Collection (ATCC).

The "protease" or "protein hydrolase" is a generic term that includes proteinase or endopeptidase that will degrade mainly protein, and peptidase degrading a small peptide.

The Koji mold having an increased capability of the secretion of a protease compared with that of its parent strain may be cultured by any method known for those skilled in the art in order to produce the protease secreted by the mold. For example, it is possible to culture the Koji mold of the present invention in a solid or liquid culture medium to make it secrete the protease into the culture medium, and collect the protease from the culture medium. Selection of culture system and culture medium, and culture conditions such as temperature and time may be optionally determined by those skilled in the art by referring to the following examples.

According to the present invention, a protein degradation product may be produced by mixing a culture material obtained by culturing the Koji mold of the present invention with a protein-containing material so as to degrade the protein in the material. There is no limitation with respect to the protein comprised in the material, including gelatin, collagen and gluten, for example. The degraded protein obtained from the material comprising gelatin, collagen and gluten may be useful as a seasoning agent.

The examples of the Koji mold introduced or transformed with the vector of the present invention, and having an increased capability of secretion of a protease compared with that of its parent strain, C001, C002, C003 and C004, were deposited at the International Patent Organism Depository of the National Institute of Advanced Industrial Science and Technology at AIST Tsukuba Central 6, 1-1, Higashi 1-chome Tsukuba-shi, Ibaraki-ken 305-8566 Japan on Sep. 9, 2005 with Accession No. FERM P-20659, FERM P-20660, FERM P-20661 and FERM P-20662, respectively, and then transferred to international deposit under Budapest Treaty on Aug. 30, 2006 with Accession No. FERM BP-10668, FERM BP-10869, FERM BP-10670 and FERM BP-10671, respectively.

The present invention will be further explained below with reference to the examples, which should not be construed to limit the scope of the present invention.

Example 1

Prediction and Extraction of a Transcriptional Regulatory Factor

A sequence that was predicted to encode a transcriptional regulatory factor was extracted based on the whole genome sequence of *Aspergillus oryzae* (Japanese Patent Application Publication No. 2005-176602) in accordance with the following steps. In these steps, detailed analysis was not carried out, but basically any gene potential as a transcriptional regulatory factor was considered as a subject to be listed.

(1) Extraction of a Sequence Predicted to be a Gene of a Transcriptional Regulatory Factor by Identity Search All of the DNA sequences predicted to be a gene sequence was extracted by means of an automated gene-prediction software form the whole genome sequence of *Aspergillus oryzae*. The thus extracted DNA sequences were named and will be referred to herein as an "automatically putative gene sequence."

Identity search was done by means of an identity search software, BLAST, using a sequence of a gene product predicted from each automatically putative gene sequence (referred to hereinafter as an "automatically putative gene product sequence") as a basic sequence for a public database of known proteins (a non-overlapped protein database by NCBI, "nr"). The information about the function of the resulting sequences was sorted, and subjected to a keyword search with respect to their information about gene function, so that the automatically putative gene sequences comprising a keyword relating to the transcriptional regulatory factor were selected.

(2) Search of a DNA Sequence Encoding an Amino Acid Sequence Predicted to be a Motif Involved in the Structure of the Transcriptional Regulatory Factor Motif search (Pfam) was carried out with respect to the automatically putative gene product sequence by using a motif search software (HMMER), so that automatically putative gene sequences encoding an amino acid sequence predicted to comprise a motif related to the transcriptional regulatory factor.

(3) Search of a DNA Sequence Having Identity with the Known Transcriptional Regulatory Factors Identity search was done by means of the identity search software, BLAST, using an amino acid sequence of known transcriptional regulatory factors of the Koji mold and other filamentous fungi as a query sequence for the above automatically putative gene product sequences. Identity search was also done by means of BLAST (tblast) using the same query sequences for genome contig sequences of the Koji mold. Accordingly, these searches made it possible to find genes that had not been automatically predicted, or genes that had been automatically predicted in a form lacking highly-conserved sequences such as a DNA-binding domain.

The above searches extracted 667 candidate genes in total from the automatically putative gene sequences (referred to hereinafter as a "candidate gene").

(Refining of the Candidate Genes and in Silico Estimation of a Gene Region)

The coding region of a gene was predicted from each candidate gene for the transcriptional regulatory factor. Prior to the prediction, the candidate genes were examined whether or not they were suitable as a subject for analysis of compulsorily expression on the basis of the information about annotation, literature information and a kind of motifs of homologous known genes and the like, so that an unsuitable one such as that functioning as a hetero complex was eliminated.

The coding region of a gene was predicted by comparison mainly with homologous known genes, using BLAST, FASTA and ALN (Bioinformatics 2000 16:190-202). When the identity with the known gene was limited and 5'-end could not be predicted, alignment information of a homologous part was prepared in order to carry out 5'-RACE. When a putative 3' end was much shorter than an original gene region, the C-terminal of a transcriptional regulatory factor would be truncated. When the putative 3'-end was much longer than the original gene region, translation seemed to terminate at an original C-terminal. Accordingly, in case where the 3'-end could not be predicted, a vector was prepared so as to integrate a region comprising even a part located sufficiently downstream of the original 3'-end, considering a length from the homologous part, positional relation with an adjacent gene, etc.

The coding region of a gene was predicted in accordance with the sequences having identity with the known genes. As a result, predicted sequences for producing a compulsory expressing strain were obtained for 300 genes in total, comprising genes whose whole sequences was predicted in silico and a part of genes whose 5'-end was identified by 5' RACE.

Example 2

Construction of an Expression Plasmid

A plasmid, pAPTLN, was constructed as an expression plasmid for the expression of a gene of a transcriptional regulatory factor in Koji mold, comprising an amylase gene promoter of *Aspergillus oryzae* and an amylase gene terminator of *Aspergillus nidulans* as the expression unit, a multi-cloning site for the insertion of the gene of the transcriptional regulatory factor, and niaD gene of *Aspergillus oryzae* as a selectable maker gene.

Spores of $5 \times 10^5$ of *Aspergillus nidulans* IAM2130 strain cultured on an agar plate were scraped and suspended in 300 μl of Nuclei Lysis Solution buffer (manufactured by Promega Corporation) in a micro tube. One gram of glass beads BZ-06 (manufactured by AS ONE Corporation) were added into the micro tube containing the suspended spores and subjected two times to the treatment with tissue lyser (manufactured by QIAGEN) for 3 min at 25 cycles/sec. The mixture was warmed for 15 min at 65° C. and allowed to stand for 5 min at a room temperature. It was mixed with 1.5 μl of RNase Solution (10 mg/ml) and warmed for one hour at 37° C. After the addition of 100 μl of Protein Precipitation Solution, it was vigorously shaken for 20 sec and centrifuged for 5 min at 13,500 rpm. A supernatant was transferred into so another micro tube, and mixed with 350 μl of isopropanol by turning the micro tube upside down, followed by centrifugation for 3 min at 12,000 rpm. The resulting precipitate was washed with 70% ethanol, dried and suspended in 100 μl of TE buffer [10 mM Tris-HCl (pH7.5), 1 mM EDTA] to obtain a genome DNA solution. Amplification of the amylase terminator gene of *Aspergillus nidulans* was carried out using the resulting genome DNA as a template and the following primers.

```
5'-gggtagtcgtacccgatgatgaaac-3'     (SEQ ID NO: 5)

5'-agcctaggccgctgcaggcag-3'         (SEQ ID NO 6)
```

PCR was carried but by means of PTC-200 (manufactured by MJ Research Co.) using TaKaRa LA Taq (TAKARA BIO INC.). The composition of a reaction solution was as follows:
(Agent: Used Amount:Final Concentration)

TaKaRa LA Taq: 0.5 μl

10×LA PCR Buffer II: 5 μl: 1×

25 mM $MgCl_2$: 5 μl: 2.5 mM dNTP Mixture: 8 μl: 0.4 mM each

Template DNA (0.5 μg): 1 μl

Primer: 1 μl×two kinds: 0.2 μM each

Sterilized water: 28.5 μl

Total liquid volume: 50 μl

The above reaction solution (50 μl) was mixed in a reaction tube (0.2 ml) and set in PTC-200 and PCR was done in the following temperature settings:

95° C., 2 min: one cycle

95° C., 30 sec; 58° C., 30 sec; 72° C., 2 min: 30 cycles

72° C., 3 min: one cycle

The reaction solution was subjected to precipitation treatment with ethanol and the resulting precipitate was suspended in 20 μl of the TE buffer. It was digested with PstI and subjected to electrophoresis with 0.7% agarose gel, so that a desired amplified product was excised. The thus excised amplified product was purified with Gel Extraction Kit (QIAGEN) to obtain the amylase gene terminator of *Aspergillus nidulans*. Plasmid pUC19 was treated with SmaI and PstI, subjected to electrophoresis with 0.7% agarose gel, so that a DNA fragment with about 2.7 kb was collected with the same kit. *Escherichia coli*. JM109 strain was transformed with a ligated product of the collected DNA fragment and the amylase gene terminator of *Aspergillus nidulans* to obtain a plasmid pAT comprising the amylase gene terminator of *Aspergillus nidulans* inserted into SmaI-PstI site in the multi-cloning site of pUC19.

The plasmid pAT was digested with SmaI and HindIII and subjected to electrophoresis with 0.7% agarose gel to collect a DNA fragment comprising the amylase gene terminator of *Aspergillus nidulans* with the same kit. A plasmid pMAR5 (Biosci. Biotech. Biochem., 56(10), 1674-1675, 1992) was digested with SmaI and HindIII and subjected to electrophoresis with 0.7% agarose gel to collect a DNA fragment lacking argB gene and the amylase gene terminator of *Aspergillus oryzae* with the same kit. *Escherichia coli* JM109 strain was then transformed with a ligated product of the two DNA fragments derived from pAT and pMAR5 to obtain a plasmid pAPT comprising the amylase promoter of *Aspergillus oryzae* and the amylase gene terminator of *Aspergillus nidulans*.

The TE buffer (100 µl) containing two kinds of synthesized DNA (100 µM each) was boiled for 5 min and cooled to a room temperature to obtain a multi-cloning site linker. The plasmid pAPT was digested with EcoRI and SmaI and subjected to electrophoresis with 0.7% agarose gel to collect a DNA fragment lacking the multi cloning site. *Escherchia coli* JM109 strain was then transformed with a ligated product of the collected DNA fragment and the multi-cloning site linker to obtain a plasmid pAPTL. A plasmid pST14 (Mol. Gen, Genet., (1989) 218:99-104) was digested with HindIII and subjected to electrophoresis with 0.7% agarose gel to collect a DNA fragment comprising niaD gene of *Aspergillus oryzae* with the same kit. A plasmid pAPTLN for the expression of a transcriptional regulatory factor gene was constructed by inserting the collected DNA fragment into HindIII site of pAPTL.

(Construction of a Recombinant Plasmid for the Expression of a Transcriptional Regulatory Factor Gene)

A gene of each transcriptional regulatory factor was obtained by PCR based on the DNA sequences that had been predicted to be the genes of interest. At first, the genome DNA of *Aspergillus oryzae* RIB40 strain was prepared. Each of the genes was obtained by means of PCR using the prepared genome DNA as a template and two kinds of primers prepared with reference to a DNA sequence located 100 bp upstream of an initiation codon of the predicted gene and a DNA sequence in the vicinity of a termination codon of the predicted gene. When the primer was prepared with reference to the DNA sequence located 100 bp upstream of an initiation codon, a restriction site was introduced, which was located in the multi-cloning site of the plasmid pAPTLN but not present in the transcriptional regulatory factor gene to be amplified. The amplified transcriptional regulatory factor gene was treated with a restriction enzyme corresponding to the above restriction site and inserted into the multi-cloning site of the plasmid pAPTLN (between the inserted restriction site and SmaI) to obtain a recombinant vector for the expression of each transcriptional regulatory factor gene.

An example of the construction of the recombinant vector for the expression of each transcriptional regulatory factor gene was shown below.

The transcriptional regulatory factor gene C001 (SEQ ID NO:1) was obtained by means of PCR using the genome DNA prepared from *Aspergillus oryzae* RIB40 strain and the following primers.

5'-atacaggcattctatcgataaaatgtttcc-3'     (SEQ ID NO: 7)

5'-gggctacatctgctgttgtagaagttgc-3'     (SEQ ID NO: 8)

PCR was carried out by means of PTC-200 (manufactured by MJ Research Co.) using TOYOBO KOD-Plus-DNA (TOYOBO CO., LTD.). The composition of a reaction solution was as follows:

(Agent: Used Amount:Final Concentration)

KOD-Plus-DNA Polymerase: 1 µl

10×PCR buffer for KOD-Plus-DNA: 5 µl: 1×

25 mM MgCl$_2$: 2 µl: 1 mM 2 mM dNTP Mixture: 5 µl: 0.2 mM each

Template DNA (0.2 µg): 1 µl

Primer: 1 µl×two kinds: 0.3 µM each

Sterilized water: 34 µl

Total liquid volume: 50 µl

The above reaction solution (50 µl) was mixed in a reaction tube (0.2 ml) and set in PTC-200 and PCR was done in the following temperature settings:

94° C., 2 min: one cycle

94° C., 15 sec; 58° C., 30 sec; 68° C., 4 min: 30 cycles

68° C., 3 min: one cycle

The reaction solution was subjected to precipitation treatment with ethanol and the resulting precipitate was suspended in 20 µl of the TE buffer. It was digested with ClaI and subjected to electrophoresis with 0.7% agarose gel, so that a desired amplified product was excised. The thus excised amplified product was purified with Gel Extraction Kit (QIAGEN) and inserted into ClaI-SmaI site in the multi-coning site of the plasmid pAPTLN to obtain a plasmid pC001 for the expression of a transcriptional regulatory factor gene C001.

By using a similar method, transcriptional regulatory factor genes C002, C003, and C004 were obtained.

The transcriptional regulatory factor gene C002 (SEQ ID NO:2) was amplified by using the following two primers having NheI restriction site introduced instead of ClaI, purified and inserted into NheI-SmaI site of the multi-cloning site of the plasmid pAPTLN.

5'-tcatacaagctagcaaaatggcggaga-3'     (SEQ ID NO: 9)

5'-gggctcgataactttttactcccgtgata-3'     (SEQ ID NO: 10)

The transcriptional regulatory factor gene C003 (SEQ ID NO:3) was amplified by using the following two primers having ClaI and SpeI restriction sites introduced, purified and inserted into ClaI-SpeI site of the multi-cloning site of the plasmid pAPTLN.

5'-ccatcgataatattagtatgctgaatga-3'     (SEQ ID NO: 11)

5'-ggactagttcaggtctttcgaatgtcagga-3'     (SEQ ID NO: 12)

The transcriptional regulatory factor gene C004 (SEQ ID NO:4) was amplified by using the following two primers having ClaI and SpeI restriction sites introduced instead of ClaI, purified and inserted into ClaI-SpeI site of the multi-cloning site of the plasmid pAPTLN.

5'-ccatcgataagtaaaaggatgttattagat-3' (SEQ ID NO: 13)

5'-ggactagtttaatccgttctcatggccgaa-3' (SEQ ID NO: 14)

Example 3

Preparation of a Koji Mold Compulsorily Expressing the Transcriptional Regulatory Factor Gene A niaD-negative strain obtained from *Aspergillus oryzae* RIB326 strain by the method described in Mol. Gen. Genet., (1989) 218:99-104 was transformed with the recombinant plasmids pC001, pC002, pC003 or pC004 for the expression of a transcriptional regulatory factor gene. The transformation was done in accordance with a method using polyethylene glycol and calcium chloride for a protoplast (Mol. Gen. Genet (1989) 218:99-104). The transformation with 5 μg of each plasmid followed by selection in a minimum essential medium gave about 200 colonies. Separation of mononuclear conidium was repeated in the minimum essential medium for 15 colonies of each plasmid so as to stabilize their characters. Southern analysis was then made using a mature region of each transcriptional regulatory factor gene so as to select a strain, which harbored the used plasmid in the transformation inserted at the niaD locus of its genome. The thus selected strains were named as C001, C002, C003 and C004, respectively. The results of Southern analysis were shown in FIG. 1.

Example 4

Method for the Culture of the Koji Mold and Determination of the Activity of an Extracellular Enzyme (1) Method for the Culture of the Koji Mold in a Gelatin Medium and Determination of the Activity of a Protein Hydrolase for Gelatin Degradation Each transformant was cultured with shaking in a liquid medium comprising gelatin and their activity of degrading gelatin was accessed by comparison of a concentration of glutamic acid in the medium with a control.

Spores of each transformant grown on an agar minimum medium were scraped with 3 ml of sterilized water, and inoculated into 40 ml of gelatin medium (2% Gelatin, 0.1% $KH_2PO_4$, 0.05% $MgSO_4$, 0.05% KCl, 0.001% $FeSO_4$ $7H_2O$, 0.3% $NaNO_3$, 3% Maltose pH6.0: $1 \times 10^7$ spores/40 ml of the gelatin medium) in a conical flask with 50 ml volume. After shaking for 115 hours at 30° C. and 150 rpm, the amount of glutamic acid in the culture supernatant was determined with YAMASA kit for the determination of L-glutamic acid (YAMASA CORPORATION). The activity of the protein hydrolase in the culture supernatant was then compared with reference to the above activity of gelatin degradation. A niaD-positive strain obtained by transformation of the niaD-negative strain of RIB 326 with the plasmid pAPTLN was cultured in each experiment as a control. The amount of glutamic acid in the culture supernatant and the activity of protein hydrolase of C004 strain, which was thought to have the highest activity of gelatin degradation, were shown as percentages for those of the control in Table 1.

TABLE 1

| Name of Strain | Amount of Glutamic Acid | Activity of Protein Hydrolase |
| --- | --- | --- |
| C004 | 511% | 501% |

(2) Method for the Culture of the Koji Mold in a Bran Medium and Comparison of the Transformants with a Wild-Type Strain of Koji Mold in the Activity of a Protein Hydrolase Bran and deionized water were mixed at the ratio of 5:4, allowed to stand for 30 min at a room temperature, dispersed 5 g each into a conical flask with 150 ml volume and sterilized for 15 min in an autoclave. The numbers of the spores of the wild-type strain of *Aspergillus oryzae* RIB326 and the compulsorily-expressing strains were calculated in advance with a hemacytometer, and the spores were inoculated into the mixture at $5 \times 10^5$ spores per 1 g of bran medium. The culture was continued for 4 days at 30° C. with mixing after the lapse of 24 and 48 hours followed by still standing until the end of the culture. After the completion of the culture, the bran medium was mixed with 50 ml of deionized water and 500 μl of toluene, shaken for 2 hours at a room temperature, and filtered through No. 2 filter paper (Advantec Co.) to give filtrate, which would be used as an enzyme solution.

The activity of the protein hydrolase was shown as a ratio to that of the wild-type strain, which was represented as "1", as calculated by the following formula:

(Ratio of the activity of the protein hydrolase)=the compulsorily expressing strain(absorbance of a sample–absorbance at a blank level)/the wild-type strain(absorbance of a sample–absorbance at a blank level). The activity of the protein hydrolase was determined as follows so as to obtain the above absorbance.

The enzyme solution (20 μl) was added to 2 ml of a substrate liquid (1% azocasein, 0.05M phosphate buffer: pH7.0) warmed to 30° C. in advance and kept for 20 min at 30° C. for reaction. The reaction was terminated by the addition of 2 ml of a reaction-stopping agent (10% trichloroacetic acid). The mixture was then allowed to stand for 20 min at 30° C. and the resulting precipitate was filtered through No. 5C filter paper (Advantec Co.). Absorbance at 410 nm of the resulting filtrate was then determined. As a blank sample, the reaction-stopping agent was added before the addition of the enzyme liquid followed by the same procedures.

Comparison of the transformants with the wild-type strain in the activity of the protein hydrolase confirmed that C002, C001 and C003 showed three times as higher activity of the protein hydrolase as that of the wild-type strain (FIG. 2). C004 showed 2.2 times as higher activity of the protein hydrolase as that of the wild-type strain.

The above results showed that the Koji mold transformed with the recombinant vector according to the present invention, C001, C002, C003 and C004, had an increased capability of the secretion of the protein hydrolase compared with that of their parent strain. The activity of the protein hydrolase was increased in a liquid medium such as the gelatin medium and a solid medium such as the bran medium, showing that industrial applicability of the present invention is very high.

The DNA sequences C001, C002, C003 and C004 are shown as SEQ ID NO:1, NO:2, NO:3 and NO:4, respectively, in which the 101th base from the beginning of each sequence is a starting base of an initiation codon, and the 101th base from the end of the sequence is the last base of a termination codon.)

The gene C001 has a Zinc finger motif of C2H2 type, and showed 81% identity with steA gene of *Aspergillus nidulans* at an amino acid level. The steA gene has been reported as a gene essential for sexual reproduction (Vallim et al., Mol. Microbiol. 36(2):290-301, (2000)).

The gene C002 has a Zinc finger motif of Zn2-Cys6 type (Fungal zinc binuclear cluster), and shows 67% identity with a functionally unidentified gene of *Aspergillus fumigatus* encoding C6 finger domain protein, putative at an amino acid level. Among genes showing identity with the gene C002, a functionally identified gene showing the highest identity with it is naf gene involved in transcription of kutinase gene of *Nectria haematococca*, showing only 31% identity at an amino acid level, though.

The gene C003 has a Zinc finger motif of Zn2-Cys6 type (Fungal zinc binuclear cluster), and shows 55% identity with a functionally unidentified gene *Aspergillus fumigatus* encoding C6 finger domain protein, putative at an amino acid level (this gene was different from the above functionally unidentified gene). Among genes showing identity with the gene C003, a functionally identified gene that shows the highest identity with it is nirA gene involved in transcription of a nitrate assimilation-related gene of *Aspergillus nidulans*, showing only 22% identity at an amino acid level, though. The identity was searched by BLAST (blastp) using nr database of NCBI.

The gene C004 has a Zinc finger motif of C2H2 type, and shows 73% identity with amdx gene of *Aspergillus nidulans* at an amino acid level. The amdX gene has been reported as a transcriptional regulatory factor of amdS gene encoding acetoamidase (Murphy et al., Mol Microbiol, 23(3):591-602, (1997)).

Accordingly, the sequences and functions of these known homologous genes never suggest the increase of the activity of the protein hydrolase by their compulsory expression.

INDUSTRIAL APPLICABILITY

The present invention is very important from an industrial point of view in the production of foods such as a seasoning, pharmaceuticals such as digestive agent, proteases for use in detergents and the like.

SEQUENCE LISTING

```
<160> NUMBER OF SEQ ID NOS: 14

<210> SEQ ID NO 1
<211> LENGTH: 2617
<212> TYPE: DNA
<213> ORGANISM: Aspergillus oryzae
<220> FEATURE:
<221> NAME/KEY: exon
<222> LOCATION: (101)..(224)
<220> FEATURE:
<221> NAME/KEY: exon
<222> LOCATION: (326)..(425)
<220> FEATURE:
<221> NAME/KEY: exon
<222> LOCATION: (490)..(2028)
<220> FEATURE:
<221> NAME/KEY: exon
<222> LOCATION: (2127)..(2210)
<220> FEATURE:
<221> NAME/KEY: exon
<222> LOCATION: (2265)..(2517)

<400> SEQUENCE: 1
cacagagttg tttcatccag cttgtcaatg ccgcttatct ttgattcaaa cattcctcta        60
gcacctgatt aatacgatat acaggcattc tctgagcaaa atg ttt ccg caa cat       115
                                             Met Phe Pro Gln His
                                             1               5 ggt gct ccc atg gca cct cct cag aaa ccg gaa aca ttc atg ctt tcg       163
Gly Ala Pro Met Ala Pro Pro Gln Lys Pro Glu Thr Phe Met Leu Ser
         10                  15                  20 aac gag gcg cag caa agc ctt cct cat gac gcg caa gtc gcg cta cag       211
Asn Glu Ala Gln Gln Ser Leu Pro His Asp Ala Gln Val Ala Leu Gln
     25                  30                  35 caa gtt gac aat t gtaagtcggg tatccttcca tagaggccgg ccgactagac        264
Gln Val Asp Asn
         40 cattctcgtc atttaacgtc aatcaacctt taaatctagg ctaatatgat tgtcgatata       324 g tg aag tac ttc ctt ctt tct gcg cca gta gac tgg caa cca gat caa       372
  Leu Lys Tyr Phe Leu Leu Ser Ala Pro Val Asp Trp Gln Pro Asp Gln
           45                  50                  55 ctc att aga cgg ttc cta ctt cct act ggc gac tac ata tct tgt gtt       420
Leu Ile Arg Arg Phe Leu Leu Pro Thr Gly Asp Tyr Ile Ser Cys Val
         60                  65                  70 cta tg gttcgtttga tcaaatataa actctagctc aggaggaagg atcgttgagc        475
Leu Trp
     75 tgatttggtg atag g aac aat ctt ttc cac atc tcg ggt acc gat att gtt    526
               Asn Asn Leu Phe His Ile Ser Gly Thr Asp Ile Val
                       80                  85 cgg tgc ctg gcc ttt aga ttt caa gcg ttc ggg cgt ccc gtg aag aat       574
```

```
            Arg Cys Leu Ala Phe Arg Phe Gln Ala Phe Gly Arg Pro Val Lys Asn
                        90                  95                 100 tcg aag aag ttc gaa gag ggt atc ttt tcc gat ctc cga aat ctc aag              622
Ser Lys Lys Phe Glu Glu Gly Ile Phe Ser Asp Leu Arg Asn Leu Lys
        105                 110                 115 gct gga aca gat gcg aca cta gaa gaa ccg aag agt cca ttc ctt gat              670
Ala Gly Thr Asp Ala Thr Leu Glu Glu Pro Lys Ser Pro Phe Leu Asp
120                 125                 130                 135 ttt ctc tat aag aac aat tgc att cga aca cag aaa aag caa aaa gtt              718
Phe Leu Tyr Lys Asn Asn Cys Ile Arg Thr Gln Lys Lys Gln Lys Val
                140                 145                 150 ttt tac tgg tat agt gtt cca cac gat cgg ctg ttt ctc gat gct ttg              766
Phe Tyr Trp Tyr Ser Val Pro His Asp Arg Leu Phe Leu Asp Ala Leu
            155                 160                 165 gaa cgt gat ttg aag cgg gag aaa atg gga caa gag gcg act aca gtc              814
Glu Arg Asp Leu Lys Arg Glu Lys Met Gly Gln Glu Ala Thr Thr Val
        170                 175                 180 gcg gtc agc gag cct gct ttg tct ttc gag ttt gat tca tct caa tcg              862
Ala Val Ser Glu Pro Ala Leu Ser Phe Glu Phe Asp Ser Ser Gln Ser
185                 190                 195 tta tat gaa cag ctc aca aag gcg caa caa gca aac tca tca tcg ttt              910
Leu Tyr Glu Gln Leu Thr Lys Ala Gln Gln Ala Asn Ser Ser Ser Phe
200                 205                 210                 215 act gca cac gca agt acg aca tat ggc caa tcc gct tcc cca gtg gtt              958
Thr Ala His Ala Ser Thr Thr Tyr Gly Gln Ser Ala Ser Pro Val Val
                220                 225                 230 cgg acc gtt gac gct atg cct cct ccc cag atg gct ccc cag atg gcc             1006
Arg Thr Val Asp Ala Met Pro Pro Pro Gln Met Ala Pro Gln Met Ala
            235                 240                 245 ccc cca acg ata tca ctc ctc ccg gac gaa tct ggc agt cca gcg att             1054
Pro Pro Thr Ile Ser Leu Leu Pro Asp Glu Ser Gly Ser Pro Ala Ile
        250                 255                 260 tac aac ccg atc cct atg ccc aat acc ctg gcg cag agc gtt gtt aag             1102
Tyr Asn Pro Ile Pro Met Pro Asn Thr Leu Ala Gln Ser Val Val Lys
265                 270                 275 cgc gag cta gat tat ggg tcg atc cag tat gat cgc aat gga atg ccc             1150
Arg Glu Leu Asp Tyr Gly Ser Ile Gln Tyr Asp Arg Asn Gly Met Pro
280                 285                 290                 295 att gct cgc gtg cat cag cgc cat gct tcc atg cca act ttc gtc gag             1198
Ile Ala Arg Val His Gln Arg His Ala Ser Met Pro Thr Phe Val Glu
                300                 305                 310 tat tca ccg gca cca tcg ttc gtt tcg tcc caa tac gaa gac tac agc             1246
Tyr Ser Pro Ala Pro Ser Phe Val Ser Ser Gln Tyr Glu Asp Tyr Ser
            315                 320                 325 aac agg gga ttg tcc ttt gaa ccc gtt acg ccc cca cag cac agt gtt             1294
Asn Arg Gly Leu Ser Phe Glu Pro Val Thr Pro Pro Gln His Ser Val
        330                 335                 340 ccg ctt ggc act gaa cca gca tat att gct aat gaa gat acc ggt ctc             1342
Pro Leu Gly Thr Glu Pro Ala Tyr Ile Ala Asn Glu Asp Thr Gly Leu
345                 350                 355 tat act gct atc cct gag atc tct gct gct gca ttc aac ccg atg ttg             1390
Tyr Thr Ala Ile Pro Glu Ile Ser Ala Ala Ala Phe Asn Pro Met Leu
360                 365                 370                 375 cag ctt ccg cca tca aat ctc gca agc gct cat ttc ccc gcc cct gca             1438
Gln Leu Pro Pro Ser Asn Leu Ala Ser Ala His Phe Pro Ala Pro Ala
                380                 385                 390 agg aca ttt cat tcg aat gtg tac tct gtt ttg gag ggt tct cca acg             1486
Arg Thr Phe His Ser Asn Val Tyr Ser Val Leu Glu Gly Ser Pro Thr
            395                 400                 405
```

-continued

| | |
|---|---|
| tac aag cag cgg cgg cgt cga tcc tcg ata ccg ccg ggc gtt aat aac<br>Tyr Lys Gln Arg Arg Arg Arg Ser Ser Ile Pro Pro Gly Val Asn Asn<br>          410                      415                      420 | 1534 |
| ccg att gct act ccc act cat act caa gcg ccg ggg ccc tct caa cca<br>Pro Ile Ala Thr Pro Thr His Thr Gln Ala Pro Gly Pro Ser Gln Pro<br>425                      430                        435 | 1582 |
| att gca tac gct gcc cac agg cca agt gat cta cgg cgc tcc gtt tct<br>Ile Ala Tyr Ala Ala His Arg Pro Ser Asp Leu Arg Arg Ser Val Ser<br>440                      445                      450                  455 | 1630 |
| agt tcg gtg gcc ccc gtc gct gag acg gaa gag cca cgt cat gaa tcg<br>Ser Ser Val Ala Pro Val Ala Glu Thr Glu Glu Pro Arg His Glu Ser<br>                460                      465                      470 | 1678 |
| tcc cgc cgt atc atg aat ggt tat ccg acg ggc gcc ctt ccg caa aag<br>Ser Arg Arg Ile Met Asn Gly Tyr Pro Thr Gly Ala Leu Pro Gln Lys<br>                    475                      480                      485 | 1726 |
| aac tta tta cac gag atg tct cgc aat ggg acg ccg ctc tca agc ctc<br>Asn Leu Leu His Glu Met Ser Arg Asn Gly Thr Pro Leu Ser Ser Leu<br>                490                      495                      500 | 1774 |
| gag gaa aac cct gag cag gct gcc atg cca ctt gcg aat ccc cct gat<br>Glu Glu Asn Pro Glu Gln Ala Ala Met Pro Leu Ala Asn Pro Pro Asp<br>505                      510                      515 | 1822 |
| gag ttg aca gcc ctt cct aat ggt gat gtt ctg gag aca ggc gcg cag<br>Glu Leu Thr Ala Leu Pro Asn Gly Asp Val Leu Glu Thr Gly Ala Gln<br>520                      525                      530                  535 | 1870 |
| cac agc gcg atg aac aaa gca gag cgg ttt gtt ccc ggc cca gtt cgc<br>His Ser Ala Met Asn Lys Ala Glu Arg Phe Val Pro Gly Pro Val Arg<br>                540                      545                      550 | 1918 |
| cgc gct cga agc gct aca atg atg gag ctt ggc cct tat cct cag aag<br>Arg Ala Arg Ser Ala Thr Met Met Glu Leu Gly Pro Tyr Pro Gln Lys<br>                    555                      560                      565 | 1966 |
| tca cat tca tgc cct atc ccg tca tgt ggg cga ctc ttc aag aga tta<br>Ser His Ser Cys Pro Ile Pro Ser Cys Gly Arg Leu Phe Lys Arg Leu<br>                570                      575                      580 | 2014 |
| gaa cat ttg aag cg  gtatgttata actatccagt gacaccacta acttttacct<br>Glu His Leu Lys Arg<br>                585 | 2068 |
| atccacttgg ccgcttcttg actgtacctg caatcgctca ctgacacttg acttgtag g | 2127 |
| cat gtg aga acc cac acc cag gaa aga ccc tac cct tgt cct tat tgc<br>His Val Arg Thr His Thr Gln Glu Arg Pro Tyr Pro Cys Pro Tyr Cys<br>                590                      595                      600 | 2175 |
| aat aaa gca ttc tcg cgc tct gac aac ctt gca ca  gtgagttaac<br>Asn Lys Ala Phe Ser Arg Ser Asp Asn Leu Ala Gln<br>605                      610                      615 | 2220 |
| taacaatgca ttgtaactga ctattatact gactatacgt atag a cac cgt cgg<br>                                                                                                    His Arg Arg | 2274 |
| atc cat gag gct caa cag gac ggc caa caa cca ctc cat gtg caa gat<br>Ile His Glu Ala Gln Gln Asp Gly Gln Gln Pro Leu His Val Gln Asp<br>620                      625                      630                      635 | 2322 |
| gaa gac ctc gaa aat gag gac aac gaa ctc ggt tcg cag gat gag gga<br>Glu Asp Leu Glu Asn Glu Asp Asn Glu Leu Gly Ser Gln Asp Glu Gly<br>                640                      645                      650 | 2370 |
| tcg tct cct tct gag tct att cca agt act gtg gtg aat gtt tcc act<br>Ser Ser Pro Ser Glu Ser Ile Pro Ser Thr Val Val Asn Val Ser Thr<br>                    655                      660                      665 | 2418 |
| gtc acg tcg atg cct tct act atg acc ctg cct tcc gcc atg cct acc<br>Val Thr Ser Met Pro Ser Thr Met Thr Leu Pro Ser Ala Met Pro Thr<br>                670                      675                      680 | 2466 |
| atg atg gca cct cac atg gtt gct ccg caa ctt cta caa cag cag atg<br>Met Met Ala Pro His Met Val Ala Pro Gln Leu Leu Gln Gln Gln Met | 2514 |

```
        685              690              695
tag aaggcatgag ggaaagtatg actccagtgg tccttttccc gattctcgtg    2567
aacattaata atgagtccga ttttgccgac catgataccc cacggtggat         2617

<210> SEQ ID NO 2
<211> LENGTH: 2861
<212> TYPE: DNA
<213> ORGANISM: Aspergillus oryzae
<220> FEATURE:
<221> NAME/KEY: exon
<222> LOCATION: (101)..(1090)
<220> FEATURE:
<221> NAME/KEY: exon
<222> LOCATION: (1425)..(1833)
<220> FEATURE:
<221> NAME/KEY: exon
<222> LOCATION: (1896)..(2761)

<400> SEQUENCE: 2
gactgcaaaa taatttcatc gattccgccc gaggccaatc aacacctggg atcattttcg    60
cgcgacagca cactttccaa agatcatacc acaaggaaaa atg gcg gag aca gca   115
                                              Met Ala Glu Thr Ala
                                              1               5 gat cct gca ggc aca ccc ggc gag ctg cca aaa cag gcc acc gag cca    163
Asp Pro Ala Gly Thr Pro Gly Glu Leu Pro Lys Gln Ala Thr Glu Pro
            10                  15                  20 acc gat acg ctg gct gca ccg acg agc acc tct gcc gaa tat tct acg    211
Thr Asp Thr Leu Ala Ala Pro Thr Ser Thr Ser Ala Glu Tyr Ser Thr
        25                  30                  35 ttt tca gct gta gac gtt tct ctt cct cct ata gat aaa tgt cta cca    259
Phe Ser Ala Val Asp Val Ser Leu Pro Pro Ile Asp Lys Cys Leu Pro
    40                  45                  50 gca atg gat acc cct ata gac aca acg ctc cca cca tta gac ccg tca    307
Ala Met Asp Thr Pro Ile Asp Thr Thr Leu Pro Pro Leu Asp Pro Ser
55                  60                  65 ata ccg tct cta ccg cca att gac aca tcc tta cct ccg ata gac act    355
Ile Pro Ser Leu Pro Pro Ile Asp Thr Ser Leu Pro Pro Ile Asp Thr
70                  75                  80                  85 acc ttg cca gct acg gac gga ggt ttg ggt aca gat acg aat ttc tcg    403
Thr Leu Pro Ala Thr Asp Gly Gly Leu Gly Thr Asp Thr Asn Phe Ser
                90                  95                  100 ttt gac gat acg gac cca aaa cct gat gac gga gga ctt ggc ggg ccg    451
Phe Asp Asp Thr Asp Pro Lys Pro Asp Asp Gly Gly Leu Gly Gly Pro
            105                 110                 115 gtg tct act gca cag gtt tcg gcg aca cct ggt agt aat att ggg gaa    499
Val Ser Thr Ala Gln Val Ser Ala Thr Pro Gly Ser Asn Ile Gly Glu
        120                 125                 130 caa ccg gga cct tca cct gcc ccc gac tct tca tgg cag ctg ccg tcc    547
Gln Pro Gly Pro Ser Pro Ala Pro Asp Ser Ser Trp Gln Leu Pro Ser
    135                 140                 145 aat ggt aca cat tcg caa cag cta cct cca ttg cag aac caa tca gcg    595
Asn Gly Thr His Ser Gln Gln Leu Pro Pro Leu Gln Asn Gln Ser Ala
150                 155                 160                 165 caa ccg caa tca cag ccg cag tat cag cag cag cag ccg cag cag cag    643
Gln Pro Gln Ser Gln Pro Gln Tyr Gln Gln Gln Gln Pro Gln Gln Gln
                170                 175                 180 caa cag caa cat gca ccc caa cag cag cat gcg cca tca cag cag tat    691
Gln Gln Gln His Ala Pro Gln Gln Gln His Ala Pro Ser Gln Gln Tyr
            185                 190                 195 caa ccc cag cag cca cag caa cag ggt caa atg caa gcg caa ccc cag    739
Gln Pro Gln Gln Pro Gln Gln Gln Gly Gln Met Gln Ala Gln Pro Gln
```

-continued

```
              200                 205                 210
tca cag caa tat cag cag cag agc tcc gac atg tat cac aac cat caa    787
Ser Gln Gln Tyr Gln Gln Gln Ser Ser Asp Met Tyr His Asn His Gln
        215                 220                 225 gct ggc tct gca tcg atg aac aca ccc tcg atg cag aca atg gat cat    835
Ala Gly Ser Ala Ser Met Asn Thr Pro Ser Met Gln Thr Met Asp His
230                 235                 240                 245 cac tct tcc cag gga cag acg tcg cat gtc cca caa gcc ccc att gga    883
His Ser Ser Gln Gly Gln Thr Ser His Val Pro Gln Ala Pro Ile Gly
                250                 255                 260 tcg cct atg ccc cca atg gct tca gta ggc caa tac atg acg gga tac    931
Ser Pro Met Pro Pro Met Ala Ser Val Gly Gln Tyr Met Thr Gly Tyr
            265                 270                 275 ccg aac aac gtt ggg caa atg gga atg aat tcg agt gcg caa atg cga    979
Pro Asn Asn Val Gly Gln Met Gly Met Asn Ser Ser Ala Gln Met Arg
        280                 285                 290 tat caa cta cca gga gat ccg aac aag atg ctc tct ggt ggc aga cac   1027
Tyr Gln Leu Pro Gly Asp Pro Asn Lys Met Leu Ser Gly Gly Arg His
    295                 300                 305 aag aag gag gtc aag cgc aga acc aag aca ggt tgt tta aca tgt cga   1075
Lys Lys Glu Val Lys Arg Arg Thr Lys Thr Gly Cys Leu Thr Cys Arg
310                 315                 320                 325 aaa cgg aga att aag gtacgtgata cgaaatataa gatcaagaag ctgtttgtcc   1130
Lys Arg Arg Ile Lys
                330 atttattgtt ggatgaggaa ctttgagcaa caggttgggg tgggcgtcgg ggaaggaaat   1190 gtgttgtggt cgcttcgctt gtgtcgcaag ctctgccttc ggctcgcctg caagaaaccc   1250 cgccattcac ggtgtcgctt gttgttgccc actgttttcc tccccgcccg acagcccaat   1310 cccgtggcct ttattattgt tttctttcct tattttttg cgtgaaaaaa tattcaatac    1370 agtccggtgt cattctttc ccctcattca cgctgacggt gggcaatact ttag tgc      1427
                                                              Cys gac gaa ggc cat ccc gtc tgc cga aac tgc gtc aaa agt aaa cgt gaa   1475
Asp Glu Gly His Pro Val Cys Arg Asn Cys Val Lys Ser Lys Arg Glu
                335                 340                 345 tgt tta ggt tac gat ccg gtg ttt aag caa cag ccg act cct tct gct   1523
Cys Leu Gly Tyr Asp Pro Val Phe Lys Gln Gln Pro Thr Pro Ser Ala
        350                 355                 360 ata cag cca gct ccg aac cca cac ccg tcg ctg gtg gtt aac ccg caa   1571
Ile Gln Pro Ala Pro Asn Pro His Pro Ser Leu Val Val Asn Pro Gln
    365                 370                 375 gat cct tct act tcg tcg tcg aca ccc aca tat cct gct gct cct ccg   1619
Asp Pro Ser Thr Ser Ser Ser Thr Pro Thr Tyr Pro Ala Ala Pro Pro
380                 385                 390                 395 ggc tac gtg cct gcg gtc tct cag cct ttt gct ccg tcc gag tct ccc   1667
Gly Tyr Val Pro Ala Val Ser Gln Pro Phe Ala Pro Ser Glu Ser Pro
                400                 405                 410 agc acg tcc acc gac aga tac gac tac ggc gcg ccc atc gat cca aca   1715
Ser Thr Ser Thr Asp Arg Tyr Asp Tyr Gly Ala Pro Ile Asp Pro Thr
        415                 420                 425 tta gac gga aac aac tct tcg aac atg gcc agt gta cag aat gct gta   1763
Leu Asp Gly Asn Asn Ser Ser Asn Met Ala Ser Val Gln Asn Ala Val
    430                 435                 440 gag ggt ggc ttg cag ccg act gtc aat cca gcg aac acc acg aca tcg   1811
Glu Gly Gly Leu Gln Pro Thr Val Asn Pro Ala Asn Thr Thr Thr Ser
445                 450                 455 tcg gac cct aca agc ttc aga g gtgcgttttt gatctaagat tccttggctt    1863
Ser Asp Pro Thr Ser Phe Arg
```

-continued

```
                                                             460                   465
cacgcccgtt cttgtgctta tattcggctt a gtg  aaa caa gtc caa att agc                         1915
                                    Val Lys Gln Val Gln Ile Ser
                                                            470 gat ctt ctg gcg ctg aga ggg att cct cct ccc cca ccc cat cct atc                         1963
Asp Leu Leu Ala Leu Arg Gly Ile Pro Pro Pro Pro Pro His Pro Ile
        475                 480                 485 act act att caa ccg aac cgt cta gaa gaa atc aaa gcc gtc ttc ctt                         2011
Thr Thr Ile Gln Pro Asn Arg Leu Glu Glu Ile Lys Ala Val Phe Leu
490                 495                 500                 505 gcc aca tat gct cct gcc att gac aag ttc ttc gag acg cgt tgg ttc                         2059
Ala Thr Tyr Ala Pro Ala Ile Asp Lys Phe Phe Glu Thr Arg Trp Phe
                510                 515                 520 cag gat acg gct ttg act cac ctt ttg gcc aat gcc cag ctt atg gcc                         2107
Gln Asp Thr Ala Leu Thr His Leu Leu Ala Asn Ala Gln Leu Met Ala
            525                 530                 535 gag tat tcg gcg tta atc gag gct ttt aac gat cag aac ctc agt gat                         2155
Glu Tyr Ser Ala Leu Ile Glu Ala Phe Asn Asp Gln Asn Leu Ser Asp
        540                 545                 550 ccg aat gtc atc gca cgg cta gaa agc ttt gaa gcg tcc gtg gtt tgg                         2203
Pro Asn Val Ile Ala Arg Leu Glu Ser Phe Glu Ala Ser Val Val Trp
555                 560                 565 agt tct atg aca ttg tgt cgt cat gtt atg aat gta tcg aat gga agt                         2251
Ser Ser Met Thr Leu Cys Arg His Val Met Asn Val Ser Asn Gly Ser
570                 575                 580                 585 cat ggc cag gat tat gat tta cta gcc gct tcg aaa cga ctg gat gtt                         2299
His Gly Gln Asp Tyr Asp Leu Leu Ala Ala Ser Lys Arg Leu Asp Val
                590                 595                 600 att gag tcc atg att aca ggc gaa cat ctg gac tcg aat ccc tta tcc                         2347
Ile Glu Ser Met Ile Thr Gly Glu His Leu Asp Ser Asn Pro Leu Ser
            605                 610                 615 cag ttt cct ccc agg gac ccg ccc aca aat ccc ccc ggt ctc tca gat                         2395
Gln Phe Pro Pro Arg Asp Pro Pro Thr Asn Pro Pro Gly Leu Ser Asp
        620                 625                 630 cag tta gcg caa cga tcg ctg gat ttt tgg tgc gca att ggc cac ttt                         2443
Gln Leu Ala Gln Arg Ser Leu Asp Phe Trp Cys Ala Ile Gly His Phe
635                 640                 645 ctt act ctt cat gat aac gag gct agt tca gcc aaa gag att gac gat                         2491
Leu Thr Leu His Asp Asn Glu Ala Ser Ser Ala Lys Glu Ile Asp Asp
650                 655                 660                 665 act ctt ggc cgt tgc cgc acg ctg ttg gat acg ttt gaa aac cgt gat                         2539
Thr Leu Gly Arg Cys Arg Thr Leu Leu Asp Thr Phe Glu Asn Arg Asp
                670                 675                 680 gtg atc tat tca att gct atc gcg cgt cat ctc gga cag cgc tgg gca                         2587
Val Ile Tyr Ser Ile Ala Ile Ala Arg His Leu Gly Gln Arg Trp Ala
            685                 690                 695 gat ttt ccg cgc agc ttc ccg cag ccc atc aca acg aac gag aag gat                         2635
Asp Phe Pro Arg Ser Phe Pro Gln Pro Ile Thr Thr Asn Glu Lys Asp
        700                 705                 710 gcc ggg gct aaa ctc tac gtt gcc caa aag ttt ctc gaa cag gaa gcg                         2683
Ala Gly Ala Lys Leu Tyr Val Ala Gln Lys Phe Leu Glu Gln Glu Ala
715                 720                 725 ggt ggg aaa ggc acc aca caa gtc atc aaa cgt att tgc ggc atg gtg                         2731
Gly Gly Lys Gly Thr Thr Gln Val Ile Lys Arg Ile Cys Gly Met Val
730                 735                 740                 745 gtg cgt tcc tgg ttc gta tca cgg gag taa aaagttatcg agatatgtct                           2781
Val Arg Ser Trp Phe Val Ser Arg Glu
                750 gacttgcatt tgatgactct ggcgtggatt ttgtaatatg gcaaaagag ccctcgcaca                        2841
```

```
<210> SEQ ID NO 3
<211> LENGTH: 2550
<212> TYPE: DNA
<213> ORGANISM: Aspergillus oryzae
<220> FEATURE:
<221> NAME/KEY: exon
<222> LOCATION: (101)..(499)
<220> FEATURE:
<221> NAME/KEY: exon
<222> LOCATION: (570)..(935)
<220> FEATURE:
<221> NAME/KEY: exon
<222> LOCATION: (986)..(1320)
<220> FEATURE:
<221> NAME/KEY: exon
<222> LOCATION: (1374)..(1724)
<220> FEATURE:
<221> NAME/KEY: exon
<222> LOCATION: (1778)..(2450)

<400> SEQUENCE: 3
```

```
ctgctggcga agctttttgg                                                 2861
```

```
tcgggcaatt cccgctctac gggctctacc acgagacgga gctatcaatg aatgatcggt      60
atcctctgcg ttcttccggt cgagtactac gaatattagt atg ctg aat gat ccc      115
                                            Met Leu Asn Asp Pro
                                            1               5 acc gac ggt gcg ctc tcg cgc ttg ggg gcg tcc ggt gtg gaa cca tct      163
Thr Asp Gly Ala Leu Ser Arg Leu Gly Ala Ser Gly Val Glu Pro Ser
            10                  15                  20 tcc gac caa gtc cag acc tct agc acg ggg aac cct aag atc cgg att      211
Ser Asp Gln Val Gln Thr Ser Ser Thr Gly Asn Pro Lys Ile Arg Ile
        25                  30                  35 ccg cgc tta ggg acc gcc ccc gtc agc gct cac cgc caa cgc acc agc      259
Pro Arg Leu Gly Thr Ala Pro Val Ser Ala His Arg Gln Arg Thr Ser
    40                  45                  50 cgg gcg tgt gcc ccg tgt cat cag agg aag acc aag tgt gac ggc caa      307
Arg Ala Cys Ala Pro Cys His Gln Arg Lys Thr Lys Cys Asp Gly Gln
55                  60                  65 aag cct caa tgc aaa cag tgt cgc caa tta ggc atc ccc tgt acc tat      355
Lys Pro Gln Cys Lys Gln Cys Arg Gln Leu Gly Ile Pro Cys Thr Tyr
70                  75                  80                  85 gtg ggg tca aag agg gaa caa caa aag tgg gcc ctg gaa tcc gtc caa      403
Val Gly Ser Lys Arg Glu Gln Gln Lys Trp Ala Leu Glu Ser Val Gln
            90                  95                  100 gcg aag atc cag tcc tat gag tcc ctg tta caa cga atc att aca gac      451
Ala Lys Ile Gln Ser Tyr Glu Ser Leu Leu Gln Arg Ile Ile Thr Asp
        105                 110                 115 agc agc gag gat cca tcc aag ttc aag ctg att gaa gaa ctg ata act      499
Ser Ser Glu Asp Pro Ser Lys Phe Lys Leu Ile Glu Glu Leu Ile Thr
    120                 125                 130 gtacgtatgt ccgtgggtca ggtatacggc caagtgttgg acgtgggaa ctatattaat      559 acgcgcccag caa cat ttt caa ggc acg ccg acg ata ctg gct ccg ctt      608
            Gln His Phe Gln Gly Thr Pro Thr Ile Leu Ala Pro Leu
                135                 140                 145 ctg gcg cta ggg tct ttg gcg gac cga agc ccg tcc ccg tcc aaa cat      656
Leu Ala Leu Gly Ser Leu Ala Asp Arg Ser Pro Ser Pro Ser Lys His
150                 155                 160 ggc tta tca ttg tac cga atg ctt gcc gcg tgg gca act cat gcc cgc      704
Gly Leu Ser Leu Tyr Arg Met Leu Ala Ala Trp Ala Thr His Ala Arg
            165                 170                 175 agt gag acc caa cca ctc gtg cag aaa cca atc atc cag ata acc gga      752
Ser Glu Thr Gln Pro Leu Val Gln Lys Pro Ile Ile Gln Ile Thr Gly
```

```
                Ser Glu Thr Gln Pro Leu Val Gln Lys Pro Ile Ile Gln Ile Thr Gly
                    180                 185                 190 att cat cat tgg acc tcg ctg gcg aac aat gac acg gcg agc cat cta          800
Ile His His Trp Thr Ser Leu Ala Asn Asn Asp Thr Ala Ser His Leu
195                 200                 205                 210 ttg tcc ctg tac ttt acg tgg gag aac ccc acc tgg caa ctg att gac          848
Leu Ser Leu Tyr Phe Thr Trp Glu Asn Pro Thr Trp Gln Leu Ile Asp
                    215                 220                 225 aag gag atg ttc gtc cgc gac ctg gaa tgt gga cat gga aag ttt tgc          896
Lys Glu Met Phe Val Arg Asp Leu Glu Cys Gly His Gly Lys Phe Cys
                230                 235                 240 tcc gca tta ttg gtt acc gta tta ctc ttt ttt ggc tgt gtacgtgtgg           945
Ser Ala Leu Leu Val Thr Val Leu Leu Phe Phe Gly Cys
            245                 250                 255 ccatcgaccg gagtgaagtg acgactaacc aggggttcag agt cta tcc tac aat         1000
                                          Ser Leu Ser Tyr Asn
                                                          260 tta gat aaa atc act gat cga cga cag gaa aag ctg ctg acc aag aat         1048
Leu Asp Lys Ile Thr Asp Arg Arg Gln Glu Lys Leu Leu Thr Lys Asn
                265                 270                 275 tta tat gcc gag ata cag cgt cta tgg gag gtc gaa aaa cac ctc aag         1096
Leu Tyr Ala Glu Ile Gln Arg Leu Trp Glu Val Glu Lys His Leu Lys
                280                 285                 290 agt ctt ccc act gcg caa tcc agt atc ctg att ggg tta ctc tgt tgc         1144
Ser Leu Pro Thr Ala Gln Ser Ser Ile Leu Ile Gly Leu Leu Cys Cys
                295                 300                 305 acc ttt ggc ctg gac aga ttt ggc acc cag tat atc atg cat ggg gct         1192
Thr Phe Gly Leu Asp Arg Phe Gly Thr Gln Tyr Ile Met His Gly Ala
            310                 315                 320 caa cta tgc cta aac tta gga ctc cag aat gag tct cca tca tac ttc         1240
Gln Leu Cys Leu Asn Leu Gly Leu Gln Asn Glu Ser Pro Ser Tyr Phe
325                 330                 335                 340 tat ggc ggc gca ccg gat gaa tat gga cac ctc gct agg tct cat aag         1288
Tyr Gly Gly Ala Pro Asp Glu Tyr Gly His Leu Ala Arg Ser His Lys
                345                 350                 355 tta gtt gcc tgg gcg gtg tac gat gtt caa gg  gtgagagacc acatattttc       1340
Leu Val Ala Trp Ala Val Tyr Asp Val Gln Gly
                360                 365 tttaaactgt tcttactaa ctcgtccaca cag c ctt gca tct caa gtt tat           1392
                                     Leu Ala Ser Gln Val Tyr
                                                     370 aga aag gta cca gcc tgg aaa gag cct ccg ccc gtg aaa ttc tcc cca         1440
Arg Lys Val Pro Ala Trp Lys Glu Pro Pro Pro Val Lys Phe Ser Pro
        375                 380                 385 atc gaa gcg gcc gga tta gat gca ggt gtt gaa tgg agt ccc tat ccg         1488
Ile Glu Ala Ala Gly Leu Asp Ala Gly Val Glu Trp Ser Pro Tyr Pro
390                 395                 400                 405 ttc gcg act cct att tcc cag cca ttc ttc ttc acg gcg gcg tgc ttc         1536
Phe Ala Thr Pro Ile Ser Gln Pro Phe Phe Phe Thr Ala Ala Cys Phe
                410                 415                 420 agg tct gac cta gtt act ata gtt cat caa att gcc aag ttt gcc ctt         1584
Arg Ser Asp Leu Val Thr Ile Val His Gln Ile Ala Lys Phe Ala Leu
                425                 430                 435 cag ttt ccc gat gcg gtc atg aac aat gat gat tgg gag tac ggc cgc         1632
Gln Phe Pro Asp Ala Val Met Asn Asn Asp Asp Trp Glu Tyr Gly Arg
                440                 445                 450 caa ttg cac caa aag ctg ctg cag tgg aag gcc acc ctg cct cct gtt         1680
Gln Leu His Gln Lys Leu Leu Gln Trp Lys Ala Thr Leu Pro Pro Val
        455                 460                 465
```

-continued

| | |
|---|---|
| ctt cta ctt gaa cat aat acc aca ccg cac gta atc tgc tta ca<br>Leu Leu Leu Glu His Asn Thr Thr Pro His Val Ile Cys Leu His<br>470                 475                       480 | 1724 |
| gttcgccatc ccctccaccg cgttgcgtcg tcagtgactg acggatatga tag t gaa<br>                                                                        Glu<br>                                                                        485 | 1781 |
| tat tac tat gca acc att gca tct cta tgc cag atc ttc tgt gca aac<br>Tyr Tyr Tyr Ala Thr Ile Ala Ser Leu Cys Gln Ile Phe Cys Ala Asn<br>                              490                           495                     500 | 1829 |
| ctg ggc tcc acg gat gac cag att tcg aat cca aaa gac ttt gat cca<br>Leu Gly Ser Thr Asp Asp Gln Ile Ser Asn Pro Lys Asp Phe Asp Pro<br>                 505                       510                       515 | 1877 |
| tac ata ata atg tcg cag gct tta gat gac atg ggg tcc ttg att ttg<br>Tyr Ile Ile Met Ser Gln Ala Leu Asp Asp Met Gly Ser Leu Ile Leu<br>        520                       525                        530 | 1925 |
| cta ttc aaa cgc tgc cac gga tgg aag tct ctt ccg gtt gtc atg ctg<br>Leu Phe Lys Arg Cys His Gly Trp Lys Ser Leu Pro Val Val Met Leu<br>535                       540                       545 | 1973 |
| cac tat ttt tgt gtc gca ggg gtt cac tca gtg tcg aag ctg aat gct<br>His Tyr Phe Cys Val Ala Gly Val His Ser Val Ser Lys Leu Asn Ala<br>550                       555                       560                     565 | 2021 |
| cat gaa ccg aag tgg agc tat atc ctg gag gac tgt gtg gtg ggc ctt<br>His Glu Pro Lys Trp Ser Tyr Ile Leu Glu Asp Cys Val Val Gly Leu<br>                 570                       575                     580 | 2069 |
| tgg cac atg agt ctg ggg tgg ggt cgt tta tgt aca gcc ttc ctc cgg<br>Trp His Met Ser Leu Gly Trp Gly Arg Leu Cys Thr Ala Phe Leu Arg<br>        585                       590                       595 | 2117 |
| acg atc gaa ctg gtt ttg aag cag aac aat ccg gac ccg tcc ctc gtg<br>Thr Ile Glu Leu Val Leu Lys Gln Asn Asn Pro Asp Pro Ser Leu Val<br>       600                       605                       610 | 2165 |
| cct tcc agg gtc gtc gag ata ttc agg aaa cta aac gag ggc gct ttg<br>Pro Ser Arg Val Val Glu Ile Phe Arg Lys Leu Asn Glu Gly Ala Leu<br>615                       620                       625 | 2213 |
| tgg acg gtg aca gac atc tca tcc cta gcg gcc gat tat gtg gtt tac<br>Trp Thr Val Thr Asp Ile Ser Ser Leu Ala Ala Asp Tyr Val Val Tyr<br>630                       635                       640                     645 | 2261 |
| acg gcc acc caa tcg gac tca agt tcg agt cca tcg tcg gct tac cgg<br>Thr Ala Thr Gln Ser Asp Ser Ser Ser Ser Pro Ser Ser Ala Tyr Arg<br>                 650                       655                       660 | 2309 |
| tac caa ggc ttg cag gat ctt atc aat gac atg gat aac ctc tct atc<br>Tyr Gln Gly Leu Gln Asp Leu Ile Asn Asp Met Asp Asn Leu Ser Ile<br>        665                       670                        675 | 2357 |
| aat cta agc tcc gaa tca ccg gag tcc ctc tca tct gtc aag gag ccc<br>Asn Leu Ser Ser Glu Ser Pro Glu Ser Leu Ser Ser Val Lys Glu Pro<br>680                       685                       690 | 2405 |
| tac gat tcc cgc agt tcc gaa gat cct gac att cga aag acc tga<br>Tyr Asp Ser Arg Ser Ser Glu Asp Pro Asp Ile Arg Lys Thr<br>        695                       700                       705 | 2450 |
| gagactattg gcagttaata tccaatgcta ctgacactat ctgggactct ttcgatacac | 2510 |
| cggggcgggg gtgcttcttt ccccatctaa gttgccgcct | 2550 |

```
<210> SEQ ID NO 4
<211> LENGTH: 3878
<212> TYPE: DNA
<213> ORGANISM: Aspergillus oryzae
<220> FEATURE:
<221> NAME/KEY: exon
<222> LOCATION: (101)..(194)
<220> FEATURE:
<221> NAME/KEY: exon
<222> LOCATION: (258)..(3632)
```

```
<220> FEATURE:
<221> NAME/KEY: exon
<222> LOCATION: (3693)..(3778)

<400> SEQUENCE: 4
ttctacactc ccctcgtttt caacttcgct cacactgcag ataacgccac ctgctaaagc         60
cggtgtctgc acgagcgatt ttgacagaga agtaaaagg atg tta tta gat aca           115
                                           Met Leu Leu Asp Thr
                                           1               5 atg gtg ggt caa gac ccg gcc act agc ccc aga acc gaa gat cta gcg          163
Met Val Gly Gln Asp Pro Ala Thr Ser Pro Arg Thr Glu Asp Leu Ala
            10                  15                  20 agt att agt gag gtt ccc gga gat atg tct g gtgagtgctt gtttacgtgg          214
Ser Ile Ser Glu Val Pro Gly Asp Met Ser
        25                  30 tgatggaaaa catctgttcc ggttcctgac caggcatcgt cag cg  ccg tcg acc          268
                                             Ala Pro Ser Thr
                                                             35 aag gaa aac aca aag aag gcc gaa aca aac ggc cag acc acg acg ccg          316
Lys Glu Asn Thr Lys Lys Ala Glu Thr Asn Gly Gln Thr Thr Thr Pro
                40                  45                  50 cag aac aac atc ccg cca ccc aag acc gat aag cct cga cct cat gtc          364
Gln Asn Asn Ile Pro Pro Pro Lys Thr Asp Lys Pro Arg Pro His Val
            55                  60                  65 tgt aca acg tgc ggt cgt tca ttt gcc cgg ctg gaa cat ctg aaa cga          412
Cys Thr Thr Cys Gly Arg Ser Phe Ala Arg Leu Glu His Leu Lys Arg
                70                  75                  80 cat gag cgc tcg cat act aaa gag aag ccc ttt gag tgc ccg gac tgt          460
His Glu Arg Ser His Thr Lys Glu Lys Pro Phe Glu Cys Pro Asp Cys
        85                  90                  95 tcg cgc tgc ttt gct cgt cgt gat ctg ctc ctg aga cac cag caa aag          508
Ser Arg Cys Phe Ala Arg Arg Asp Leu Leu Leu Arg His Gln Gln Lys
100                 105                 110                 115 cta cat atg acc acc acc ccg tcg tcg cga ccc aga aat gcc cgg aga          556
Leu His Met Thr Thr Thr Pro Ser Ser Arg Pro Arg Asn Ala Arg Arg
                120                 125                 130 gaa agc acg gga gcc gcg ggg acg ggg acg aac agg gtg cgc aag aac          604
Glu Ser Thr Gly Ala Ala Gly Thr Gly Thr Asn Arg Val Arg Lys Asn
            135                 140                 145 tcc atc gtc aat gcg tcc agc aac atg cgc ccc aga gcc aat acc att          652
Ser Ile Val Asn Ala Ser Ser Asn Met Arg Pro Arg Ala Asn Thr Ile
        150                 155                 160 agc cat att gat ggc gct tct ctg gga ctg ccc aat gcc acc cac ccc          700
Ser His Ile Asp Gly Ala Ser Leu Gly Leu Pro Asn Ala Thr His Pro
165                 170                 175 tcg cca gcg gca ccc acc cac ggc cat gcc tac cat ccg agt cta ggc          748
Ser Pro Ala Ala Pro Thr His Gly His Ala Tyr His Pro Ser Leu Gly
                180                 185                 190                 195 tca gca ccg gtg ggg tcc aat ctg gat tat cgc ggg ttc agc tcc gcc          796
Ser Ala Pro Val Gly Ser Asn Leu Asp Tyr Arg Gly Phe Ser Ser Ala
                200                 205                 210 cat ccc ccg gtg aat ggt ctg acg aag ttg gaa acc cat gga cta ccg          844
His Pro Pro Val Asn Gly Leu Thr Lys Leu Glu Thr His Gly Leu Pro
            215                 220                 225 atg gat ctt tcc ggt ggg ttg cgt acg gcc ccg gta tat ggt agc ttc          892
Met Asp Leu Ser Gly Gly Leu Arg Thr Ala Pro Val Tyr Gly Ser Phe
        230                 235                 240 gat gtc agc ctg gga gat atg ttc atg ggt cac agt acc atc aac ccc          940
Asp Val Ser Leu Gly Asp Met Phe Met Gly His Ser Thr Ile Asn Pro
245                 250                 255
```

-continued

```
gcc caa tta cac ttt ggc ggt tcg ccc caa ggg tac gga aac gat tcg      988
Ala Gln Leu His Phe Gly Gly Ser Pro Gln Gly Tyr Gly Asn Asp Ser
260                 265                 270                 275
cct tcc tca cca tac acc cag ggt gcc cat cag atg ccg ccc aca gat     1036
Pro Ser Ser Pro Tyr Thr Gln Gly Ala His Gln Met Pro Pro Thr Asp
                280                 285                 290
cct atg atg gag gat gac ttc agc ttt gat tgg atg aac gga ttc gat     1084
Pro Met Met Glu Asp Asp Phe Ser Phe Asp Trp Met Asn Gly Phe Asp
            295                 300                 305
cca tcc atg cag atg ggg aaa ggt aac gag tcg gta att gac gaa tca     1132
Pro Ser Met Gln Met Gly Lys Gly Asn Glu Ser Val Ile Asp Glu Ser
        310                 315                 320
tcg ccc tcg gcg atg agc act ggc agc cag agt ggc atc agt gaa gcc     1180
Ser Pro Ser Ala Met Ser Thr Gly Ser Gln Ser Gly Ile Ser Glu Ala
    325                 330                 335
atg atg gac gga ggg cac cgc tac tcc gtg tca tca gcg agc tgg cac     1228
Met Met Asp Gly Gly His Arg Tyr Ser Val Ser Ser Ala Ser Trp His
340                 345                 350                 355
aac ccg ttt cca ccc cac act gga ccg ccg tcc aac caa ttc att gac     1276
Asn Pro Phe Pro Pro His Thr Gly Pro Pro Ser Asn Gln Phe Ile Asp
                360                 365                 370
tac aca tct ccc act ttt aat gat cta gga att ccc ccg gaa act gtt     1324
Tyr Thr Ser Pro Thr Phe Asn Asp Leu Gly Ile Pro Pro Glu Thr Val
            375                 380                 385
tca ccc aag tct ctg atg gcg caa aac ccg ttt gct gaa agc tat gcc     1372
Ser Pro Lys Ser Leu Met Ala Gln Asn Pro Phe Ala Glu Ser Tyr Ala
        390                 395                 400
acc cct ccc tcc atg acc tcg gtg ggc cag ccc atg gta ggg gga cat     1420
Thr Pro Pro Ser Met Thr Ser Val Gly Gln Pro Met Val Gly Gly His
    405                 410                 415
tcg cag agt atg tta tca tcc tct atg gca acc aac gga gac tct cct     1468
Ser Gln Ser Met Leu Ser Ser Ser Met Ala Thr Asn Gly Asp Ser Pro
420                 425                 430                 435
aat cct ttc aac cta cct ttc gcg aat agt gcc cta cga act cac cat     1516
Asn Pro Phe Asn Leu Pro Phe Ala Asn Ser Ala Leu Arg Thr His His
                440                 445                 450
tcc tca agt tca acc gat acc ttt aca gac tcc acc cga cag gct tta     1564
Ser Ser Ser Ser Thr Asp Thr Phe Thr Asp Ser Thr Arg Gln Ala Leu
            455                 460                 465
cta gcc agc atg gcc caa ccc acc ggt ttc aac cac cgc aaa tat tct     1612
Leu Ala Ser Met Ala Gln Pro Thr Gly Phe Asn His Arg Lys Tyr Ser
        470                 475                 480
cag cca gct agc ggc atg ctt cac tgc cgt gac ctc ttt ttg cgc tct     1660
Gln Pro Ala Ser Gly Met Leu His Cys Arg Asp Leu Phe Leu Arg Ser
    485                 490                 495
tcc agc ttc aac agt tcc agc ccg ctg ccc agc act tcc gat atg cag     1708
Ser Ser Phe Asn Ser Ser Ser Pro Leu Pro Ser Thr Ser Asp Met Gln
500                 505                 510                 515
cgt tat atc tca gct tac atc acc tat ttc cac ccg cac atg ccc ttt     1756
Arg Tyr Ile Ser Ala Tyr Ile Thr Tyr Phe His Pro His Met Pro Phe
                520                 525                 530
ctc cat atc ccg acc ctc gat ttc caa gcc ccc gag tac acg aat aat     1804
Leu His Ile Pro Thr Leu Asp Phe Gln Ala Pro Glu Tyr Thr Asn Asn
            535                 540                 545
cta cga acc ccc agc ggc cat ctc aat cta agt tcg act ggt gtt gcc     1852
Leu Arg Thr Pro Ser Gly His Leu Asn Leu Ser Ser Thr Gly Val Ala
        550                 555                 560
ggc ggt ggt ggc tgt ttg atc ctc tcc atg gca gcc atc ggt gcg ctc     1900
Gly Gly Gly Gly Cys Leu Ile Leu Ser Met Ala Ala Ile Gly Ala Leu
```

-continued

```
                565                 570                 575
tac gaa tac gac acc gcg gcc tcc aaa gac ctc ttc gaa gcc gct aaa       1948
Tyr Glu Tyr Asp Thr Ala Ala Ser Lys Asp Leu Phe Glu Ala Ala Lys
580                 585                 590                 595 aag atg atc cag ctt tac cta gaa gaa cgt cgg aaa gca gac atg tcc       1996
Lys Met Ile Gln Leu Tyr Leu Glu Glu Arg Arg Lys Ala Asp Met Ser
                600                 605                 610 gcc gct ttt agc cgg gcc aat tct gcc cgc gac aac tcg gtc cac aac       2044
Ala Ala Phe Ser Arg Ala Asn Ser Ala Arg Asp Asn Ser Val His Asn
            615                 620                 625 act cca ctc tgg ttg gtg cag gcg atg ctt ttg aac gtc att tac ggc       2092
Thr Pro Leu Trp Leu Val Gln Ala Met Leu Leu Asn Val Ile Tyr Gly
        630                 635                 640 cat acc tgc ggc gac aag acc tcc gct gac atc gcg agt acg cac tgt       2140
His Thr Cys Gly Asp Lys Thr Ser Ala Asp Ile Ala Ser Thr His Cys
    645                 650                 655 gca gcc tta gtc agc ctt gct cga gcc gca gag ttg acg cat cat cta       2188
Ala Ala Leu Val Ser Leu Ala Arg Ala Ala Glu Leu Thr His His Leu
660                 665                 670                 675 gat gcg aga gat ctg cct cag gat tat ctc aaa gcc ggg ctt ggt agt       2236
Asp Ala Arg Asp Leu Pro Gln Asp Tyr Leu Lys Ala Gly Leu Gly Ser
                680                 685                 690 aga gat agt tct caa gac gcc agt cca gat cct gag acc tgg gcc tcc       2284
Arg Asp Ser Ser Gln Asp Ala Ser Pro Asp Pro Glu Thr Trp Ala Ser
            695                 700                 705 tcc atg ggc cca ccg agg gag cga aag gat tgg ttg gat tgg aaa ata       2332
Ser Met Gly Pro Pro Arg Glu Arg Lys Asp Trp Leu Asp Trp Lys Ile
        710                 715                 720 gtc gag gaa cgg aag cgt act ctt tat gcc atc ttc act ctc tcc tgc       2380
Val Glu Glu Arg Lys Arg Thr Leu Tyr Ala Ile Phe Thr Leu Ser Cys
    725                 730                 735 ttc ctt gtg tcc gct tac aac cat gct cct gcg ttg acc aat tct gaa       2428
Phe Leu Val Ser Ala Tyr Asn His Ala Pro Ala Leu Thr Asn Ser Glu
740                 745                 750                 755 att cgc ctg gac ctt cca tgc gag gag gat ctc tgg gca gca gag tcg       2476
Ile Arg Leu Asp Leu Pro Cys Glu Glu Asp Leu Trp Ala Ala Glu Ser
                760                 765                 770 cct caa gcg tgg aga aag aag ggc ggg ccc ctt gca tcc caa aag ggc       2524
Pro Gln Ala Trp Arg Lys Lys Gly Gly Pro Leu Ala Ser Gln Lys Gly
            775                 780                 785 ctg tcc ttt cct tcg gct ctg acg acg ctt ttg acc gcc agc caa cgg       2572
Leu Ser Phe Pro Ser Ala Leu Thr Thr Leu Leu Thr Ala Ser Gln Arg
        790                 795                 800 gag caa agt caa tcg cag aca cca acc agc aac aat act aca tcg gaa       2620
Glu Gln Ser Gln Ser Gln Thr Pro Thr Ser Asn Asn Thr Thr Ser Glu
    805                 810                 815 gat tct tca aac aac gat cta aag ccc agc acg ttt ggc tgc ctc gtg       2668
Asp Ser Ser Asn Asn Asp Leu Lys Pro Ser Thr Phe Gly Cys Leu Val
820                 825                 830                 835 ctg atc tac gct ctc cat aac tac att tgg gag act cgt cag cga cac       2716
Leu Ile Tyr Ala Leu His Asn Tyr Ile Trp Glu Thr Arg Gln Arg His
                840                 845                 850 atg ggc cga cag tgg acc gcc cgg gaa acc gat gcc atg caa gca cac       2764
Met Gly Arg Gln Trp Thr Ala Arg Glu Thr Asp Ala Met Gln Ala His
            855                 860                 865 att gag cca gct tta cgg gcg tgg cag gct gct tgg gcg agc aac cct       2812
Ile Glu Pro Ala Leu Arg Ala Trp Gln Ala Ala Trp Ala Ser Asn Pro
        870                 875                 880 gtc cac agt ttg gag cgg ccg aat cca ttt ggg gca ggt cct ctt tcg       2860
```

```
                    Val His Ser Leu Glu Arg Pro Asn Pro Phe Gly Ala Gly Pro Leu Ser
                        885                 890                 895 gca gat agt ata cca ttg cta gac ctg gct tac gtt cga ctg ttt gtt    2908
Ala Asp Ser Ile Pro Leu Leu Asp Leu Ala Tyr Val Arg Leu Phe Val
900                 905                 910                 915 aat cta ggt cgc tgc aaa gaa gcc ttc tgg caa cgt gat tgg aat gcc    2956
Asn Leu Gly Arg Cys Lys Glu Ala Phe Trp Gln Arg Asp Trp Asn Ala
                920                 925                 930 atg tcg gac gag ctc gcg cga ggg act gac atc gtc aat cac gtg gaa    3004
Met Ser Asp Glu Leu Ala Arg Gly Thr Asp Ile Val Asn His Val Glu
            935                 940                 945 gag att cct ccg gat gtg ttg gat ccg tcg atc acg gaa agc gtc ttt    3052
Glu Ile Pro Pro Asp Val Leu Asp Pro Ser Ile Thr Glu Ser Val Phe
        950                 955                 960 cac atg gac aac cgt cgt gat tca gtg gca gac ctt ggg gta gct gac    3100
His Met Asp Asn Arg Arg Asp Ser Val Ala Asp Leu Gly Val Ala Asp
    965                 970                 975 ctt gcc ata tcc aaa act cct acg caa gag cat ccg atg cag acc ctg    3148
Leu Ala Ile Ser Lys Thr Pro Thr Gln Glu His Pro Met Gln Thr Leu
980                 985                 990                 995 atg ggc gta cac cgt ccg ggc cag tca aag cgc gag agg cat tta        3193
Met Gly Val His Arg Pro Gly Gln Ser Lys Arg Glu Arg His Leu
                    1000                1005                1010 cgg aaa gca gct ttc tat gca gca gac tca atc tct atg tca gac        3238
Arg Lys Ala Ala Phe Tyr Ala Ala Asp Ser Ile Ser Met Ser Asp
                1015                1020                1025 cgg ctc ggg aat act ttc gcg gaa ttt aca tgc cga gac ttg ccc        3283
Arg Leu Gly Asn Thr Phe Ala Glu Phe Thr Cys Arg Asp Leu Pro
            1030                1035                1040 att caa tgc gca atg tgt act ttt gac tgc gcg caa gtc ctt gcc        3328
Ile Gln Cys Ala Met Cys Thr Phe Asp Cys Ala Gln Val Leu Ala
        1045                1050                1055 gag tgg att aca act gtg cag gag cgg gtg ggc ccc tac ttg ggg        3373
Glu Trp Ile Thr Thr Val Gln Glu Arg Val Gly Pro Tyr Leu Gly
    1060                1065                1070 ctg cta ggg cgg gac gaa gtt gac ctg gtc caa gct tcg agg gtc        3418
Leu Leu Gly Arg Asp Glu Val Asp Leu Val Gln Ala Ser Arg Val
1075                1080                1085 atg ttg cta gag gag gag gat tgt aag ctc ctg gag aag atc aag        3463
Met Leu Leu Glu Glu Glu Asp Cys Lys Leu Leu Glu Lys Ile Lys
                    1090                1095                1100 gag ata ctc gcc agt gtt gaa acc aag atg caa gcg gag gta caa        3508
Glu Ile Leu Ala Ser Val Glu Thr Lys Met Gln Ala Glu Val Gln
                1105                1110                1115 acc agt gcg act gta tct acc ctg agc gtc tta caa cgg ctg cct        3553
Thr Ser Ala Thr Val Ser Thr Leu Ser Val Leu Gln Arg Leu Pro
            1120                1125                1130 agc gtt gtg gaa ggg gga tat ggt tgc aag att ctg att gcc acg        3598
Ser Val Val Glu Gly Gly Tyr Gly Cys Lys Ile Leu Ile Ala Thr
        1135                1140                1145 gca agc ctt ttg gac agg gct gct gtc tgg cca g gtgagttcaa           3642
Ala Ser Leu Leu Asp Arg Ala Ala Val Trp Pro
    1150                1155 tttcatgcca tatgactcgc ataattcaga caaaactaac tatcggccag tc acg      3697
                                                            Val Thr aag ctc atg gct cga tct ctc gaa gcg caa gct atg cga ctg aag        3742
Lys Leu Met Ala Arg Ser Leu Glu Ala Gln Ala Met Arg Leu Lys
    1160                1165                1170 gag cgc gct gaa aat tcg gcc atg aga acg gat taa atcaaccggt         3788
Glu Arg Ala Glu Asn Ser Ala Met Arg Thr Asp
```

```
Glu Arg  Ala Glu Asn Ser Ala  Met Arg Thr Asp
    1175             1180 ctgagtggtc cattatcctt ctgcttcctt ttgtatctac ctgctcttga ggtttcacaa    3848
ccttgtataa ggttacgtgg ccttgttcgc                                     3878

<210> SEQ ID NO 5
<211> LENGTH: 25
<212> TYPE: DNA
<213> ORGANISM: Artificial sequence
<220> FEATURE:
<223> OTHER INFORMATION: Synthetic primer for amylase terminator region

<400> SEQUENCE: 5
gggtagtcgt acccgatgat gaaac                                          25

<210> SEQ ID NO 6
<211> LENGTH: 21
<212> TYPE: DNA
<213> ORGANISM: Artificial sequence
<220> FEATURE:
<223> OTHER INFORMATION: Synthetic primer for amylase terminator region

<400> SEQUENCE: 6
agcctaggcc gctgcaggca g                                              21

<210> SEQ ID NO 7
<211> LENGTH: 30
<212> TYPE: DNA
<213> ORGANISM: Artificial sequence
<220> FEATURE:
<223> OTHER INFORMATION: Synthetic primer for CO01

<400> SEQUENCE: 7
atacaggcat tctatcgata aaatgtttcc                                     30

<210> SEQ ID NO 8
<211> LENGTH: 28
<212> TYPE: DNA
<213> ORGANISM: Artificial sequence
<220> FEATURE:
<223> OTHER INFORMATION: Synthetic primer for CO01

<400> SEQUENCE: 8
gggctacatc tgctgttgta gaagttgc                                       28

<210> SEQ ID NO 9
<211> LENGTH: 27
<212> TYPE: DNA
<213> ORGANISM: Artificial sequence
<220> FEATURE:
<223> OTHER INFORMATION: Synthetic primer for CO02

<400> SEQUENCE: 9
tcatacaagc tagcaaaatg gcggaga                                        27

<210> SEQ ID NO 10
<211> LENGTH: 29
<212> TYPE: DNA
<213> ORGANISM: Artificial sequence
<220> FEATURE:
<223> OTHER INFORMATION: Synthetic primer for CO02

<400> SEQUENCE: 10
gggctcgata acttttact cccgtgata                                       29
```

```
<210> SEQ ID NO 11
<211> LENGTH: 28
<212> TYPE: DNA
<213> ORGANISM: Artificial sequence
<220> FEATURE:
<223> OTHER INFORMATION: Synthetic primer for CO03

<400> SEQUENCE: 11
ccatcgataa tattagtatg ctgaatga                                       28

<210> SEQ ID NO 12
<211> LENGTH: 30
<212> TYPE: DNA
<213> ORGANISM: Artificial sequence
<220> FEATURE:
<223> OTHER INFORMATION: Synthetic primer for CO03

<400> SEQUENCE: 12
ggactagttc aggtctttcg aatgtcagga                                     30

<210> SEQ ID NO 13
<211> LENGTH: 30
<212> TYPE: DNA
<213> ORGANISM: Artificial sequence
<220> FEATURE:
<223> OTHER INFORMATION: Synthetic primer for CO04

<400> SEQUENCE: 13
ccatcgataa gtaaaaggat gttattagat                                     30

<210> SEQ ID NO 14
<211> LENGTH: 30
<212> TYPE: DNA
<213> ORGANISM: Artificial sequence
<220> FEATURE:
<223> OTHER INFORMATION: Synthetic primer for CO04

<400> SEQUENCE: 14
ggactagttt aatccgttct catggccgaa                                     30
```

What is claimed is:

1. A recombinant vector comprising a DNA consisting of a nucleotide sequence selected from the group consisting of SEQ ID NO:1, SEQ ID NO:2, SEQ ID NO:3, and SEQ ID NO:4.

2. A recombinant vector comprising a DNA
   (a) that hybridizes under stringent conditions comprising 600 mM sodium concentration, a pH of 8, and a temperature of 68° C. with a DNA consisting of a nucleotide sequence selected from the group consisting of SEQ ID NO:1, SEQ ID NO:2, SEQ ID NO:3, and SEQ ID NO:4, and
   (b) that encodes a polypeptide capable of increasing the secretion of a protease in an *Aspergillus* host cell transformed with the vector.

3. A recombinant vector comprising a DNA consisting of a nucleotide sequence that has at least 95% identity to a DNA sequence selected from the group consisting of SEQ ID NO:1, SEQ ID NO:2, SEQ ID NO:3, and SEQ ID NO:4, and that encodes a polypeptide capable protein having a capability of increasing the secretion of a protease in an *Aspergillus* host cell transformed with the vector.

4. An *Aspergillus* cell transformed with the recombinant vector of any of claims 1, 2, or 3, whereby the transformed *Aspergillus* host cell has an increased capability of secreting a protease compared with that of the untransformed *Aspergillus* cell.

5. A method for the production of a protease, comprising culturing the transformed *Aspergillus* cell of claim 4 in a solid or liquid culture medium under conditions suitable for secretion of the protease into the culture medium, and collecting the protease from the culture medium.

6. A method for the production of a protein degradation product, comprising mixing a culture material obtained by culturing the transformed *Aspergillus* cell of claim 4 with a protein-containing material, thereby degrading the protein in the material.

7. A method for the production of a seasoning composition, comprising mixing a culture material obtained by culturing the transformed *Aspergillus* cell of claim 4 with a gelatin-containing material, thereby degrading the gelatin in the material.

8. An isolated DNA of the following (a), (b) or (c);
   (a) a DNA consisting of a nucleotide sequence selected from the group consisting of SEQ ID NO:1, SEQ ID NO:2, SEQ ID NO:3, and SEQ ID NO:4;
   (b) a DNA that hybridizes under stringent conditions comprising 600 mM sodium concentration, a pH of 8, and a temperature of 68° C. with a DNA consisting of a nucleotide sequence complementary to the DNA (a), and that encodes a polypeptide capable of increasing the secretion of a protease in an *Aspergillus* host cell;

(c) a DNA consisting of a nucleotide sequence that has at least 95% identity to a DNA sequence selected from the group consisting of SEQ ID NO:1, SEQ ID NO:2, SEQ ID NO:3, and SEQ ID NO:4, and that encodes a polypeptide capable of increasing the secretion of a protease in an *Aspergillus* host cell.

9. An isolated protein of the following (a) or (b):

(a) a protein consisting of an amino acid sequence encoded by the entire length of a DNA consisting of a nucleotide sequence selected from the group consisting of SEQ ID NO:1, SEQ ID NO:2, SEQ ID NO:3, and SEQ ID NO:4;

(b) a protein consisting of an amino acid sequence of (a) wherein one amino acid residue is replaced, deleted, or added, and wherein the protein is capable of increasing the secretion of a protease in an *Aspergillus* host cell.

* * * * *